(12) United States Patent
Starzewski et al.

(10) Patent No.: US 6,191,241 B1
(45) Date of Patent: Feb. 20, 2001

(54) METHOD FOR PRODUCING HIGH MELTING-POINT POLYOLEFINS

(75) Inventors: Karl-Heinz Aleksander Ostoja Starzewski, Bad Vilbel (DE); Warren Mark Kelly, Airdrie (CA); Andreas Stumpf, Leverkusen (DE)

(73) Assignee: Bayer Aktiengesellschaft, Leverkusen (DE)

( * ) Notice: Under 35 U.S.C. 154(b), the term of this patent shall be extended for 0 days.

This patent is subject to a terminal disclaimer.

(21) Appl. No.: 09/214,399

(22) PCT Filed: Feb. 7, 1997

(86) PCT No.: PCT/EP97/03461

§ 371 Date: Dec. 30, 1998

§ 102(e) Date: Dec. 30, 1998

(87) PCT Pub. No.: WO98/01485

PCT Pub. Date: Jan. 15, 1998

(30) Foreign Application Priority Data

Jul. 5, 1996 (DE) ............................................... 196 27 064
Apr. 5, 1997 (DE) ............................................... 197 14 058

(51) Int. Cl.$^7$ ...................................................... C08F 4/44
(52) U.S. Cl. ........................... 526/161; 526/160; 526/943; 526/352; 526/348.6; 502/152
(58) Field of Search .................................. 526/160, 161, 526/943, 351, 352, 348.6, 352.2

(56) References Cited

U.S. PATENT DOCUMENTS 5,756,417 * 5/1998 De Boer et al. ..................... 502/117

FOREIGN PATENT DOCUMENTS 0 638 593 A1 * 2/1995 (EP) .

* cited by examiner

Primary Examiner—David W. Wu
Assistant Examiner—R. Harlan

(74) Attorney, Agent, or Firm—Joseph C. Gil; Noland J. Cheung

(57) ABSTRACT

High-melting polyolefins can be prepared in bulk, in solution, in suspension or in the gas phase, the catalysts employed being metallocene compounds or π complex compounds of the formula

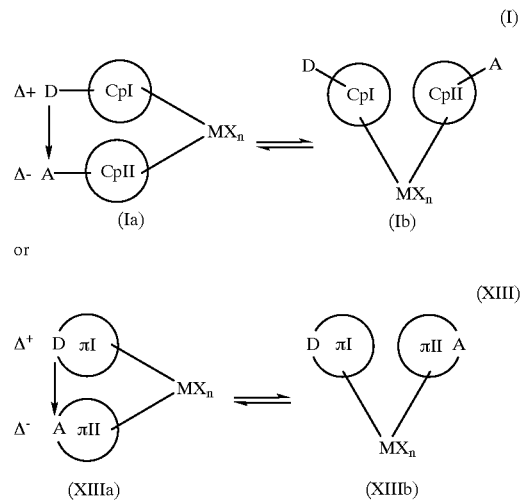

in which
 CpI and CpII represent carbanions having a cyclopentadienyl-containing structure,
 πI and πII represent charged or electrically neutral π systems,
 D represents a donor atom and
 A represents an acceptor atom,
  where D and A are linked by a reversible coordinate bond such that the donor groups assumes a positive (part) charge and the acceptor group assumes a negative (part) charge,
 M represents a transition metal of sub-group III, IV, V or VI of the Periodic Table of the Elements (Mendeleev), including the lanthanides and the actinides,
 X denotes one anion equivalent and
 n denotes the number zero, one, two, three or four, depending on the charge of M.

24 Claims, No Drawings

METHOD FOR PRODUCING HIGH MELTING-POINT POLYOLEFINS

FIELD OF THE INVENTION

The present invention relates to the use of π systems or of metallocene compounds in which a transition metal with two o systems, and in particular with aromatic π systems, such as anionic cyclopentadienyl ligands (carbanions) is complexed and the two systems are bonded reversibly to one another by at least one bridge of a donor and an acceptor, as organometallic catalysts in a process for the preparation of high-melting polyolefins by homo- or copolymerization of one or more monomers from the group consisting of optionally substituted α-olefins having two or more C atoms. The coordinate bond formed between the donor atom and the acceptor atom produces a positive (part) charge in the donor group and a negative (part) charge in the acceptor group:

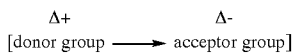

BACKGROUND OF THE INVENTION

Metallocenes and their use as catalysts in the polymerization of olefins have been known for a long time (EP-A 129 368 and the literature cited therein). It is furthermore known from EP-A '368 that metallocenes in combination with aluminum-alkyl/water as cocatalysts are active systems for the polymerization of ethylene (thus, for example, methylaluminoxane=MAO is formed from 1 mol of trimethylaluminum and 1 mol of water. Other stoichiometric ratios have also already been used successfully (WO 94/20506)). Metallocene in which the cyclopentadienyl skeletons are linked to one another covalently via a bridge are also already known. An example of the numerous patents and applications in this field which may be mentioned is EP-A 704 461, in which the linkage group mentioned therein is a (substituted) methylene group or ethylene group, a silylene group, a substituted silylene group, a substituted germylene group or a substituted phosphine group. The bridged metallocenes are also envisaged as polymerization catalysts for olefins in EP '461. In spite of the numerous patents and applications in this field, there continues to be a demand for improved catalysts which are distinguished by a high activity, so that the amount of catalyst remaining in the polymer can be set to a low level, and which are suitable for the polymerization and copolymerization of olefins.

SUMMARY OF THE INVENTION

It has now been found that particularly advantageous catalysts can be prepared from bridged X complex compounds, and in particular from metallocene compounds, in which the bridging of the two π systems is established by one, two or three reversible donor-acceptor bonds, in which in each case a coordinate or so-called dative bond which is overlapped at least formally by an ionic bond forms between the donor atom and the acceptor atom, and in which one of the donor or acceptor atoms can be part of the particular associated π system. The reversibility of the donor-acceptor bond also allows, in addition to the bridged state identified, by the arrow between D and A, the non-bridged state in which the two π systems can rotate against one another, for example through an angle of 360°, as a result of their inherent rotational energy, without the integrity of the metal complex being surrendered. When the rotation is complete, the donor-acceptor bond "snaps in" again. If several donors and/or acceptors are present, such "snapping in" can already take place after angles of less than 360° have been passed through. π systems according to the invention which are to be employed, for example metallocenes, can therefore be represented by just a double arrow and the formula parts (Ia) and (Ib) or (XIIIa) and (XIIIb) to include both states.

DETAILED DESCRIPTION OF THE INVENTION

The invention accordingly relates to a process for the preparation of high-melting polyolefins by homo- or copolymerization of one or more monomers from the group consisting of optionally substituted α-olefins having 2 or more C atoms in the presence of organometallic catalysts which can be activated by cocatalysts, which comprises employing as the organometallic catalysts metallocene compounds of the formula

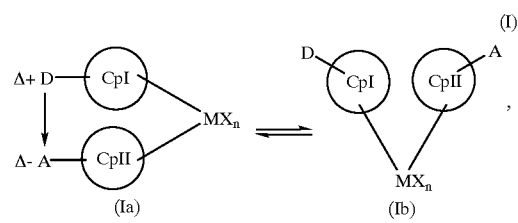

in which

CpI and CpII are two identical or different carbanions having a cyclopentadienyl-containing structure, in which one to all the H atoms can be replaced by identical or different radicals from the group consisting of linear or branched $C_1$–$C_{20}$-alkyl, which can be monosubstituted to completely substituted by halogen, mono- to trisubstituted by phenyl or mono- to trisubstituted by vinyl, $C_6$–$C_{12}$-aryl, halogenoaryl having 6 to 12 C atoms, organometallic substituents, such as silyl, trimethylsilyl or ferrocenyl, and 1 or 2 can be replaced by D and A, D denotes a donor atom, which can additionally carry substituents and has at least one free electron pair in its particular bond state, A denotes an acceptor atom, which can additionally carry substituents and has an electron pair gap in its particular bond state, where D and A are linked by a reversible coordinate bond such that the donor group assumes a positive (part) charge and the acceptor group assumes a negative (part) charge, M represents a transition metal of sub-group III, IV, V or VI of the Periodic Table of the Elements (Mendeleev), including the lanthanides and actinides, X denotes one anion equivalent and n denotes the number zero, one, two, three or four, depending on the charge of M, or π complex compounds, and in particular metallocene compounds of the formula

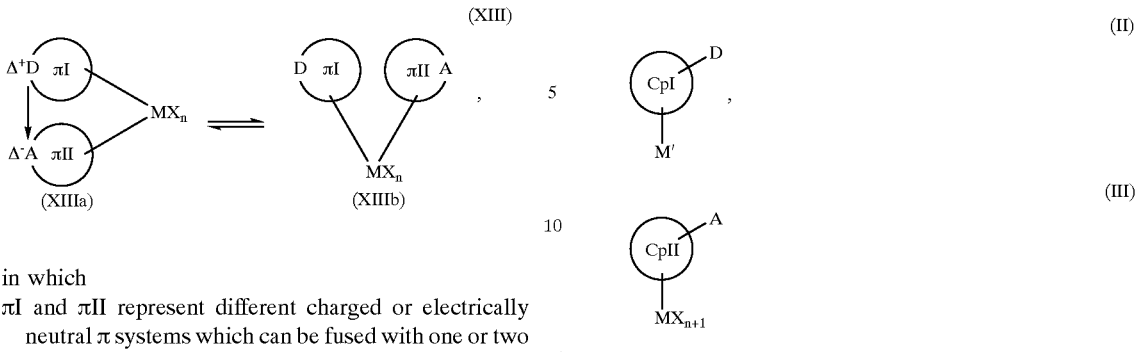

in which
- πI and πII represent different charged or electrically neutral π systems which can be fused with one or two unsaturated or saturated five- or six-membered rings,
- D denotes a donor atom, which is a substituent of πI or part of the π system of πI and has at least one free electron pair in its particular bond state,
- A denotes an acceptor atom, which is a substituent of πII or part of the π system of πII and has an electron pair gap in its particular bond state,
  - where D and A are linked by a reversible coordinate bond such that the donor group assumes a positive (part) charge and the acceptor group assumes a negative (part) charge, and where at least one of D and A is part of the particular associated π system,
  - where D and A in their turn can carry substituents,
  - where each π system and each fused-on ring system can contain one or more D or A or D and A and
  - wherein πI and πII in the non-fused or in the fused form, one to all the H atoms of the π system independently of one another can be substituted by identical or different radicals from the group consisting of linear or branched $C_1$–$C_{20}$-alkyl, which can be monosubstituted to completely substituted by halogen, mono- to tri-substituted by phenyl or mono- to trisubstituted by vinyl, $C_6$–$C_{12}$-aryl, halogenoaryl having 6 to 12 C atoms, organometallic substituents, such as silyl, trimethylsilyl or ferrocenyl, or one or two can be replaced by D and A, so that the reversible coordinate D→A bond (i) is formed between D and A, which are both parts of the particular π system or the fused-on ring system, or (ii) of which D or A is part of the π system or of the fused-on ring system and in each case the other is substituent of the non-fused π system or the fused-on ring system,
- M and X have the above meaning and
- n denotes the number zero, one, two, three or four, depending on the charges of M and those of π-I and π-II.
- π systems according to the invention are substituted and unsubstituted ethylene, allyl, pentadienyl, benzyl, butadiene, benzene, the cyclopentadienyl anion and the species which result by replacement of at least one C atom by a heteroatom.

Among the species mentioned, the cyclic species are preferred. The nature of the coordination of such ligands (π systems) to the metal can be of the s type or of the π type.

Such metallocene compounds of the formula (I) which are to be employed according to the invention can be prepared by reacting with one another either in each case a compound of the formulae (II) and (III)

or in each case a compound of the formulae (IV) and (V)

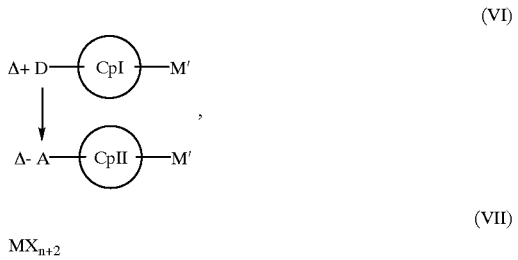

or in each case a compound of the formulae (VI) and (VII)

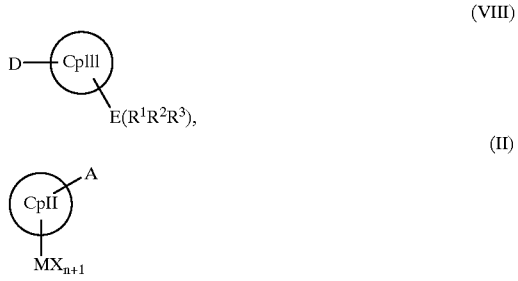

with elimination of M'X, in the presence of an aprotic solvent, or in each case a compound of the formulae (VIII) and (III)

or in each case a compound of the formulae (IV) and (IX)

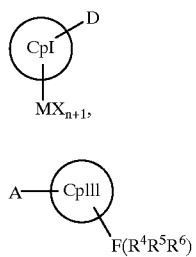
(IV)

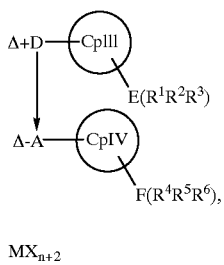
(IX)

or in each case a compound of the formulae (X) and (VII)

(X)

$\Delta+D$—CpIII
   $E(R^1R^2R^3)$
$\Delta-A$—CpIV
   $F(R^4R^5R^6)$, (VII)

$MX_{n+2}$ with elimination of $E(R^1R^2R^3)X$ and $F(R^4R^5R^6)X$, in the absence or in the presence of an aprotic solvent, in which
  CpI, CpII, D, A, M, X and n have the above meaning,
  CpIII and CpIV represent two identical or different non-charged molecular parts having a cyclopentadiene-containing structure, but are otherwise the same as CpI and CpII,
  M' denotes one cation equivalent of an alkali metal or alkaline earth metal or Tl,
  E and F independently of one another denote one of the elements Si, Ge or Sn and
  $R^1$, $R^2$, $R^3$, $R^4$, $R^5$ and $R^6$ independently of one another represent straight-chain or branched $C_1$–$C_{20}$-alkyl, $C_6$–$C_{12}$-aryl, $C_1$–$C_6$-alkyl-$C_6$–$C_{12}$-aryl, $C_6$–$C_{12}$-aryl-$C_1$–$C_6$-alkyl, vinyl, allyl or halogen,
  and where furthermore, in the formulae (VIII), (IX) and (X), hydrogen can replace $E(R^1R^2R^3)$ and $F(R^4R^5R^6)$, and in this case X can also represent an amide anion of the type $R_2N^-$ or a carbanion of the type $R_3C^-$ or an alcoholate anion of the type $RO^\ominus$, and where it is furthermore possible to react compounds of the formulae (II) or (VIII) directly with a transition metal compound of the formula (VII) in the presence of compounds of the formulae (V) or (IX).

In the reaction of (VIII) with (III) or (IV) with (IX) or (X) with (VII), in the case of the variant mentioned last, the structure (I) forms with elimination of amine $R_2NH$ or $R_2NE(R^1R^2R^3)$ or $R_2NF(R^4R^5R^6)$ or a hydrocarbon compound of the formula $R_3CH$ or $R_3CE(R^1R^2R^3)$ or $R_3CF(R^4R^5R^6)$ or an ether $ROE(R^1R^2R^3)$ or $ROF(R^4R^5R^6)$, in which the organic radicals R are identical or different and independently of one another are $C_1$–$C_{20}$-alkyl, $C_6$–$C_{12}$-aryl, substituted or unsubstituted allyl, benzyl or hydrogen. Examples of the amine or hydrocarbon, ether, silane, stannane or germane eliminated are, for example, dimethylamine, diethylamine, di-(n-propyl)-amine, di-(isopropyl)-amine, di-(tert-butyl)-amine, tert-butylamine, cyclohexylamine, aniline, methyl-phenyl-amine, di-(allyl)-amine or methane, toluene, trimethylsilylamine, trimethylsilyl ether, tetramethylsilane and the like.

It is also possible to react compounds of the formulae (II) or (VIII) directly with a transition metal compound of the formula (VII) in the presence of compounds of the formulae (V) or (IX).

π complex compounds of the formula (XIII) in which the π systems are cyclic and aromatic (metallocenes) can be prepared analogously, the following compounds being employed accordingly:

(IIa)

(IIIa)

(IVa)

(Va)

(VIa)

(VII)

$MX_{n+2}$,

(VIIIa)

(IIIa)

(IVa)

(IXa)

(Xa)

$MX_{n+2}$.    (VII)

Open-chain π complex compounds are prepared by processes known to the expert with incorporation of donor and acceptor groups.

According to the invention, for homo- or copolymerization of one or more optionally substituted α-olefins as monomers, the reaction is carried out in the gas, solution, high pressure or slurry phase at −60 to +250° C., preferably 0 to 200° C., under 0.5 to 5000, preferably 1 to 3000 bar, in the presence or absence of saturated or aromatic hydrocarbons or of saturated or aromatic halogeno-hydrocarbons and in the presence or absence of hydrogen, the metallocene compounds or the π complex compounds being employed as catalysts in an amount of $10^1$ to $10^{12}$ mol of all the monomers per mole of metallocene or π complex compound, and it being furthermore possible to carry out the reaction in the presence of Lewis acids, Brönstedt acids or Pearson acids, or additionally in the presence of Lewis bases.

Such Lewis acids are, for example, boranes or alanes, such as aluminum-alkyls, aluminum halides, aluminum alcoholates, organoboron compounds, boron halides, boric acid esters or compounds of boron or aluminum which contain both halide and alkyl or aryl or alcoholate substituents, and mixtures thereof, or the triphenylmethyl cation. Aluminoxane or mixtures of aluminum-containing Lewis acids with water are particularly preferred. According to current knowledge, all the acids act as ionizing agents which form a metallocenium cation, the charge of which is compensated by a bulky, poorly coordinating anion.

According to the invention, the reaction products of such ionizing agents with metallocene compounds of the formula (I) can furthermore be employed. They can be described by the formulae (XIa) to (XId)

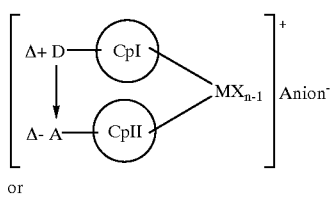

(XIa)

or

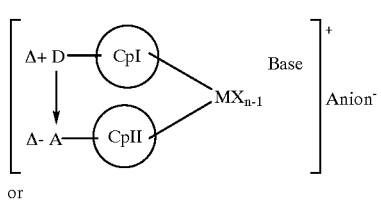

(XIb)

or

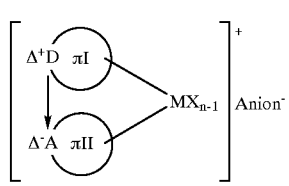

(XIc)

or

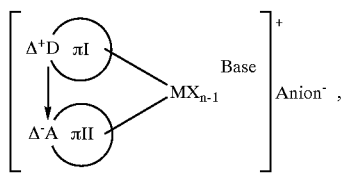

(XId)

in which
Anion represents the entire bulky, poorly coordinating anion and Base represents a Lewis base.

The catalysts of the formulae (I) and (XIII) which can be employed according to the invention can be present both in monomeric and in dimeric or oligomeric form.

It is also possible to employ a plurality of D/A catalysts simultaneously, in order to establish a certain profile of the properties of the material. Accordingly, it is also possible to employ one or more D/A catalysts in combination with other metallocenes which contain no D/A bridge.

Examples of poorly coordinating anions are, for example, $B(C_6H_5)_4^\ominus$, $B(C_6F_5)_4^\ominus$, $B(CH_3)(C_6F_5)_3^\ominus$,

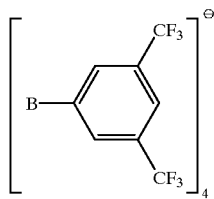

or sulfonates, such as tosylates or triflates, tetrafluoroborates, hexafluorophosphates or -antimonates, perchlorates, and voluminous cluster molecular anions of the carborane type, for example $C_2B_9H_{12}^\ominus$ or $CB_{11}H_{12}^\ominus$. If such anions are present, metallocene compounds can also act as highly active polymerization catalysts in the absence of aluminoxane. This is the case, above all, if one X ligand represents an alkyl group, allyl or benzyl. However, it may also be advantageous to employ such metallocene complexes with voluminous anions in combination with aluminum-alkyls, such as $(CH_3)_3Al$, $(C_2H_5)_3Al$, (n-/i-propyl)$_3$Al, (n-/t-butyl)$_3$Al, (i-butyl)$_3$Al, the isomeric pentyl-, hexyl- or octylaluminum-alkyls or lithium-alkyls, such as methyl-Li, benzyl-Li or butyl-Li, or the corresponding organo-Mg compounds, such as Grignard compounds, or organo-Zn compounds. Such metal-alkyls on the one hand transfer alkyl groups to the central metal, and on the other hand scavenge water or catalyst poisons from the reaction medium or monomer during polymerization reactions. Metal-alkyls of the type described can also advantageously be employed in combination with aluminoxane cocatalysts, for example in order to reduce the amount of aluminoxane required. Examples of boron compounds with which, when used, such anions are introduced are:

triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate, N,N-dimethyl(2,4,6-trimethylanilinium) tetraphenylborate,
trimethylammonium tetrakis(pentafluorophenyl)borate, triethylammonium tetrakis(pentafluorophenyl)borate,
tripropylammonium tetrakis(pentafluorophenyl)borate,
tri(n-butyl)ammonium tetrakis(pentafluorophenyl)borate, tri(sec-butyl)ammonium tetrakis(pentafluorophenyl) borate,
N,N-dimethylanilinium tetrakis(pentafluorophenyl) borate,
N,N-diethylanilinium tetrakis(pentafluorophenyl)borate, N,N-dimethyl(2,4,5-trimethylanilinium) tetrakis (pentafluorophenyl)borate,
trimethylammonium tetrakis(2,3,4,6-tetrafluorophenyl) borate,
triethylammonium tetrakis(2,3,4,6-tetrafluorophenyl) borate,
tripropylammonium tetrakis(2,3,4,6-tetrafluorophenyl) borate,
tri(n-butyl)ammonium tetrakis(2,3,4,6-tetrafluorophenyl) borate,
dimethyl(t-butyl)ammonium tetrakis(2,3,4,6-tetrafluorophenyl)borate,
N,N-dimethylanilinium tetrakis(2,3,4,6-tetrafluorophenyl)borate,
N,N-diethylanilinium tetrakis(2,3,4,6-tetrafluorophenyl) borate and
N,N-dimethyl(2,4,6-trimethylanilinium) tetrakis(2,3,4,6-tetrafluorophenyl)borate; dialkylammmonium salts, such as:
di(i-propyl)ammonium tetrakis(pentafluorophenyl) borate and
dicyclohexylammonium tetrakis(pentafluorophenyl) borate;
tri-substituted phosphonium salts, such as:
triphenylphosphonium tetrakis(pentafluorophenyl) borate,
tri(o-tolyl)phosphonium tetrakis(pentafluorophenyl) borate and
tri(2,6-dimethylphenyl)phosphonium tetrakis (pentafluorophenyl)borate;
tritolylmethyl tetrakis(pentafluorophenyl)borate,
triphenylmethyl-tetraphenylborate (trityl-tetraphenylborate),
trityl tetrakis(pentafluorophenyl)borate,
silver tetrafluoroborate,
tris(pentafluorophenyl)borane and
tris(trifluoromethyl)borane.

The metallocene compounds to be employed according to the invention and the π complex compounds can be employed in isolated form as the pure substances for the (co)polymerization. However, it is also possible to produce them and use them "in situ" in the (co)polymerization reactor in a manner known to the expert.

The first and the second carbanion CpI and CpII having a cyclopentadienyl skeleton can be identical or different. The cyclopentadienyl skeleton can be, for example, one from the group consisting of cyclopentadiene, substituted cyclopentadiene, indene, substituted indene, fluorene and substituted fluorene. 1 to 4 substituents may be present per cyclopentadiene or fused-on benzene ring. These substituents can be $C_1$–$C_{20}$-alkyl, such as methyl, ethyl, propyl, isopropyl, butyl or iso-butyl, hexyl, octyl, decyl, dodecyl, hexadecyl, octadecyl or eicosyl, $C_1$–$C_{20}$-alkoxy, such as methoxy, ethoxy, propoxy, isopropoxy, butoxy or iso-butoxy, hexoxy, octyloxy, decyloxy, dodecyloxy, hexadecyloxy, octadecyloxy, eicosyloxy, halogen, such as fluorine, chlorine or bromine, $C_6$–$C_{12}$-aryl, such as phenyl, $C_1$–$C_4$-alkylphenyl, such as tolyl, ethylphenyl, (i-) propylphenyl, (i-, tert-)butylphenyl or xylyl, halogenophenyl, such as fluoro-, chloro- or bromophenyl, naphthyl or biphenylyl, triorganyl-silyl, such as trimethylsilyl (TMS), ferrocenyl and D or A, as defined above. Fused-on aromatic rings can furthermore be partly or completely hydrogenated, so that only the double bond of which both the fused-on ring and the cyclopentadiene ring have a portion remains. Benzene rings, such as in indene or fluorene, can furthermore contain one or two further fused-on benzene rings. The cyclopentadiene or cyclopentadienyl ring and a fused-on benzene ring can also furthermore together contain a further fused-on benzene ring.

In the form of their anions, such cyclopentadiene skeletons are excellent ligands for transition metals, each cyclopentadienyl carbanion of the optionally substituted form mentioned compensating a positive charge of the central metal in the complex. Individual examples of such carbanions are cyclopentadienyl, methylcyclopentadienyl, 1,2-dimethyl-cyclopentadienyl, 1,3-dimethyl-cyclopentadienyl, indenyl, phenylindenyl, 1,2-diethyl-cyclopentadienyl, tetramethyl-cyclopentadienyl, ethyl-cyclopentadienyl, n-butyl-cyclopentadienyl, n-octyl-cyclopentadienyl, β-phenylpropyl-cyclopentadienyl, tetrahydroindenyl, propyl-cyclopentadienyl, t-butylcyclopentadienyl, benzyl-cyclopentadienyl, diphenylmethyl-cyclopentadienyl, trimethylgermyl-cyclopentadienyl, trimethylstannyl-cyclopentadienyl, trifluoromethyl-cyclopentadienyl, trimethylsilyl-cyclopentadienyl, pentamethylcyclopentadienyl, fluorenyl, tetrahydro- and octahydro-fluorenyl, fluorenyls and indenyls which are benzo-fused on the six-membered ring, N,N-dimethylamino-cyclopentadienyl, dimethylphosphino-cyclopentadienyl, methoxy-cyclopentadienyl, dimethylboranyl-cyclopentadienyl and (N,N-dimethylaminomethyl)-cyclopentadienyl.

In addition to the first donor-acceptor bond between D and A which is obligatorily present, further donor-acceptor bonds can be formed if additional D and/or A are present as substituents of the particular cyclopentadiene systems or substituents or parts of the π systems. All donor-acceptor bonds are characterized by their reversibility described above. In the case of a plurality of D and A, these can occupy various positions of those mentioned. The invention accordingly relates both to the bridged molecular states (Ia) and (XIIIa) and to the non-bridged states (Ib) and (XIIIb). The number of D groups can be identical to or different from the number of A groups. Preferably, CpI and CpII are linked via only one donor-acceptor bridge.

In addition to the D/A bridges according to the invention, covalent bridges can also be present. In these cases, the D/A bridges intensify the stereorigidity and the heat stability of the catalyst. By changing between the closed and open D/A bond, sequence polymers are accessible in the case of copolymers of different chemical composition.

The π complex compounds are likewise characterized by the presence of at least one coordinate bond between donor atom(s) D and acceptor atom(s) A. Both D and A here can be substituents of their particular π systems πI and πII or part of the π system, but always at least one of D and A is part of the π system. π system here is understood as meaning the entire π system, which is optionally fused once or twice. The following embodiments result from this:

D is part of the π system, A is a substituent of the π system;

D is a substituent of the π system, A is part of the π system;

D and A are part of their particular π system.

The following heterocyclic ring systems in which D or A is part of the ring system may be mentioned as examples:

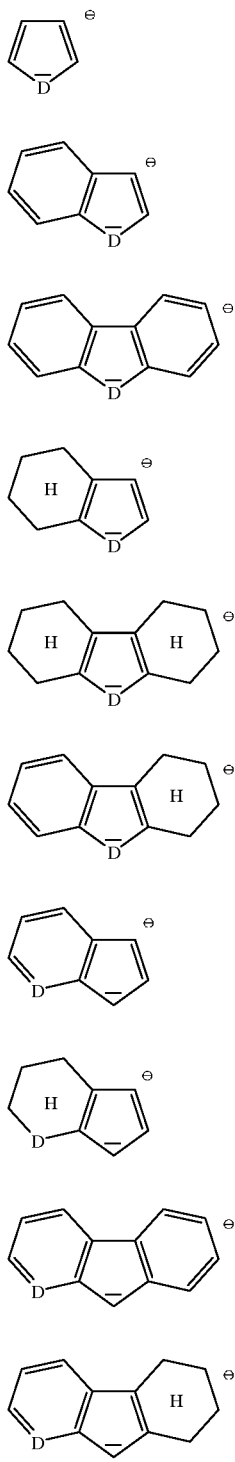

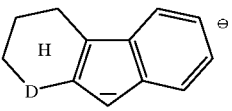
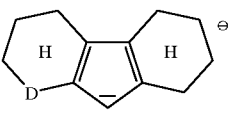
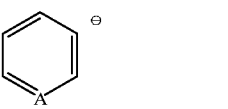
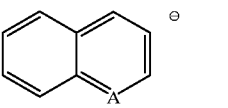
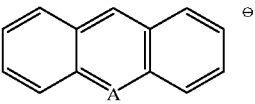
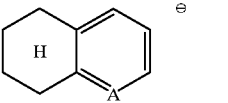
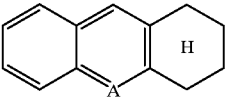
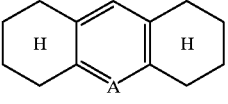

Important heterocyclic ring systems are the systems labeled (a), (b), (c), (d), (g), (m), (n) and (o); those labeled (a), (b), (c) and (m) are particularly important.

In the case where one of D and A is a substituent of an associated ring system, the ring system is 3-, 4-, 5-, 6-, 7- or 8-membered with or without an electric charge, and can be further substituted and/or fused in the manner described. 5- and 6-membered ring systems are preferred. The negatively charged cyclopentadienyl system is particularly preferred.

The first and the second π system πI and πII respectively, if it is formed as a ring system, can correspond to CpI and CpII respectively in the case where one of D and A is a substituent of the ring system.

Possible donor groups are, above all, those in which the donor atom D is an element of main group 5, 6 or 7, preferably 5 or 6, of the Periodic Table of the Elements (Mendeleev) and has at least one free electron pair, and where the donor atom in the case of elements of main group 5 is in a bond state with substituents, and in the case of elements of main group 6 can be in such a state; donor atoms of main group 7 carry no substituents. This is illustrated by the example of phosphorus P, oxygen O and chlorine Cl as donor atoms as follows, where "subst." represents those substituents mentioned and "—Cp" represents the bond to the cyclopentadienyl-containing carbanion, a line with an arrow has the meaning of a coordinate bond given in formula (I), and other lines denote electron pairs present:

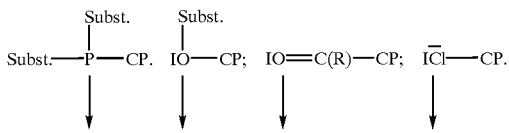

Possible acceptor groups are, above all, those in which the acceptor atom A is an element from main group 3 of the Periodic Table of the Elements (Mendeleev), such as boron, aluminum, gallium, indium and thallium, is in a bond state with substituents and has an electron gap.

D and A are linked by a coordinate bond, where D assumes a positive (part) charge and A assumes a negative (part) charge.

A distinction is accordingly being made between the donor atom D and the donor group and between the acceptor atom A and the acceptor group. The coordinate bond D→A is established between the donor atom D and acceptor atom A. The donor group denotes the unit consisting of the donor atom D, the substituent optionally present and the electron pairs present; the acceptor correspondingly denotes the unit of the acceptor atom A, the substituents and the electron gap present.

The bond between the donor atom or the acceptor atom and the cyclopentadienyl-containing carbanions can be interrupted by spacer groups in the manner of D—spacer—Cp or A—spacer—Cp. In the third of the above formula examples, =C(R)—represents such a spacer between O and Cp. Such spacer groups are, for example:

dimethylsilyl, diethysilyl, di-n-propylsilyl, diisopropylsilyl, di-n-butylsilyl, di-t-butylsilyl, d-n-hexylsilyl, methylphenylsilyl, ethylmethylsilyl, diphenylsilyl, di-(p-t-butylphenylsilyl), n-hexylmethylsilyl, cyclpentamethylsilyl, cyclotetramethylsilyl, cyclotrimethylenesilyl, dimethylgermanyl, diethylgermanyl, phenylamino, t-butylamino, methyl amino, t-butylphosphino, ethylphosphino, phenylphosphino, methylene, dimethylmethylene (i-propylidene), diethylmethylene, ethylene, dimethylethylene, diethylethylene, dipropylethylene, propylene, dimethylpropylene, diethylpropylene, 1,1-dimethyl-3,3-dimethylpropylene, teramethyldisiloxane, 1,1,4,4-tetramethylsilylethylene, diphenylmethylene.

D and A are preferably bonded to the cyclopentadienyl-containing carbanion with-out a spacer.

D and A independently of one another can be on the cyclopentadiene (or -dienyl) ring or a fused-on benzene ring or on another substituent of CpI and CpII respectively or πI and πII respectively. In the case of a plurality of D and A, these can occupy various positions of those mentioned.

Substituents on the donor atoms N, P, As, Sb, Bi, O, S, Se and Te and on the acceptor atoms B, Al, Ga, In and Tl are, for example: $C_1$–$C_{12}$(cyclo)alkyl, such as methyl, ethyl, propyl, i-propyl, cyclopropyl, butyl, i-butyl, tert-butyl, cyclobutyl, pentyl, neopentyl, cyclopentyl, hexyl, cyclohexyl and the isomeric heptyls, octyls, nonyls, decyls, undecyls and dodecyls; the $C_1$–$C_{12}$-alkoxy groups which correspond to these; vinyl, butenyl and allyl; $C_6$–$C_{12}$-aryl, such as phenyl, naphthyl or biphenylyl and benzyl, which can be substituted by halogen, 1 or 2 $C_1$–$C_4$-alkyl groups, $C_1$–$C_4$-alkoxy groups, nitro or halogenoalkyl groups, $C_1$–$C_6$-alkyl-carboxyl, $C_1$–$C_6$-alkyl-carbonyl or cyano (for example perfluorophenyl, m,m'-bis(trifluoromethyl)-phenyl and analogous substituents familiar to the expert); analogous aryloxy groups; indenyl; halogen, such as F, Cl, Br and I, 1-thienyl, disubstituted amino, such as ($C_1$–$C_{12}$-alkyl)$_2$amino, and diphenylamino, tris-($C_1$–$C_{12}$-alkyl)-silyl, NaSO$_3$-aryl, such as NaSO$_3$-phenyl and NaSO$_3$-tolyl, and $C_6H_5$—C≡C—; aliphatic and aromatic $C_1$–$C_{20}$-silyl, the alkyl substituents of which can additionally be octyl, decyl, dodecyl, stearyl or eicosyl, in addition to those mentioned above, and the aryl substituents of which can be phenyl, tolyl, xylyl, naphthyl or biphenylyl; and those substituted silyl groups which are bonded to the donor atom or the acceptor atom via —CH$_2$—, for example (CH$_3$)$_3$SiCH$_2$—; and ($C_1$–$C_{12}$-alkyl)(phenyl)-amino, ($C_1$–$C_{12}$-alkylphenyl)$_2$amino, $C_6$–$C_{12}$-aryloxy with the abovementioned aryl groups, $C_1$–$C_8$-perfluoroalkyl and perfluorophenyl. Preferred substituents are: $C_1$–$C_6$-alkyl, $C_5$–$C_6$-cycloalkyl, phenyl, tolyl, $C_1$–$C_6$-alkoxy, $C_6$–$C_{12}$-aryloxy, vinyl, allyl, benzyl, perfluorophenyl, F, Cl, Br, di-($C_1$–$C_6$-alkyl)-amino and diphenylamino.

Donor groups are those in which the free electron pair is located on the N, P, As, Sb, Bi, O, S, Se, Te, F, Cl, Br and I; of these, N, P, O and S are preferred. Examples of donor groups which may be mentioned are: (CH$_3$)$_2$N—, (C$_2$H$_5$)$_2$N—, (C$_3$H$_7$)$_2$N—, (C$_4$H$_9$)$_2$N—, (C$_6$H$_5$)$_2$N—, (CH$_3$)$_2$P—, (C$_2$H$_5$)$_2$P—, (C$_3$H$_7$)$_2$P—, (i—C$_3$H$_7$)$_2$P—, (C$_4$H$_9$)$_2$P—, (t—C$_4$H$_9$)$_2$P—, (cyclohexyl)$_2$P—, (C$_6$H$_5$)$_2$P—, CH$_3$O—, CH$_3$S—, C$_6$H$_5$S—, —C(C$_6$H$_5$)=O, —C(CH$_3$)=O, —OSi(CH$_3$)$_3$ and —OSi(CH$_3$)$_2$-t-butyl, in which N and P each carry a free electron pair and O and S each carry two free electron pairs, and where in the last two examples mentioned, the double-bonded oxygen is bonded via a spacer group, and systems such as the pyrrolidone ring, where the ring members other than N also act as spacers.

Acceptor groups are those in which an electron pair gap is present on B, Al, Ga, In or Tl, preferably B or Al; examples which may be mentioned are (CH$_3$)$_2$B—, (C$_2$H$_5$)$_2$B—, H$_2$B—, (C$_6$H$_5$)$_2$B—, (CH$_3$)(C$_6$H$_5$)B—, (vinyl)$_2$B—, (benzyl)$_2$B—, Cl$_2$B—, (CH$_3$O)$_2$B—, Cl$_2$Al—, (CH$_3$)Al—, (i—C$_4$H$_9$)$_2$Al—, (Cl)(C$_2$H$_5$)$_2$Al—, (CH$_3$)$_2$Ga—, (C$_3$H$_7$)$_2$Ga—, ((CH$_3$)$_3$Si—CH$_2$)$_2$Ga—, (vinyl)$_2$Ga—, (C$_6$H$_5$)$_2$Ga—, (CH$_3$)$_2$In—, ((CH$_3$)$_3$Si—CH$_2$)$_2$In—, (cyclopentadienyl)$_2$In—.

Those donor and acceptor groups which contain chiral centers or in which 2 substituents form a ring with the D or A atom are furthermore possible. Examples of these are, for example,

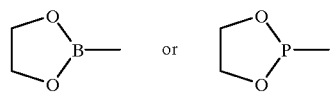

Preferred donor-acceptor bridges between CpI and CpII are, for example, the following:

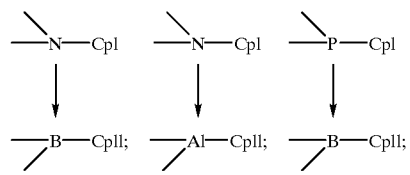

-continued

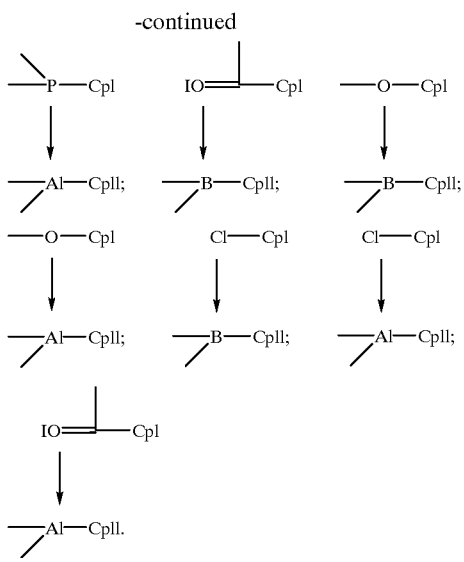

One or both π systems πI and/or πII can be present as a heterocyclic ring in the form of the above ring systems (a) to (r). D here is preferably an element of main group 5 or 6 of the Periodic Table of the Elements (Mendeleev); A here is preferably boron. Some examples of such hetero-π systems, in particular heterocyclic compounds, are:

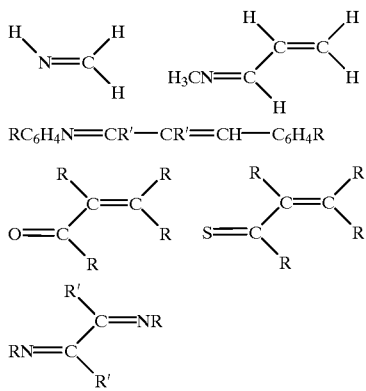

R and R'=H, alkyl, aryl or aralkyl, for example methyl, ethyl, t-butyl, phenyl or o,o'-(di-i-propyl)-phenyl.

Examples of heterocyclic radicals are: pyrrolyl, methylpyrrolyl, dimethylpyrrolyl, trimethylpyrrolyl, tetramethylpyrrolyl, t-butylpyrrolyl, di-t-butylpyrrolyl, indolyl, methylindolyl, dimethylindolyl, t-butylindolyl, di-t-butylindolyl, tetramethylphospholyl, tetraphenylphospholyl, triphenylphospholyl, trimethylphospholyl, phosphaindenyl, dibenzophospholyl (phosphafluorenyl) and dibenzopyrrolyl.

Preferred donor-acceptor bridges between πI and πII are, for example, the following: N→B, N→Al, P→B, P→Al, O→B, O→Al, Cl→B, Cl→Al, C=O→B and C=O→Al, where both atoms of these donor-acceptor bridges can be part of a hetero-π system or one atom (donor or acceptor) is part of a π system and the other is a substituent of the second π system, or where both atoms are substituents of their particular ring and one of the rings additionally contains a heteroatom.

According to the above depiction, the two ligand systems πI and πII can be linked by one, two or three donor-acceptor bridges. This is possible since, according to the invention, formula (Ia) contains the D→A bridge described, but the ligand systems πI and πII can carry further D and A as substituents or hetero-π centers; the number of resulting additional D→A bridges is zero, one or two. The number of D and A substituents on πI and πII respectively can be identical or different. The two ligand systems πI and πII can additionally be bridged covalently. (Examples of covalent bridges are described above as spacer groups.) However, compounds without a covalent bridge, in which πI and πII accordingly are linked only via a donor-acceptor bridge, are preferred.

M represents a transition metal from sub-group 3, 4, 5 or 6 of the Periodic Table of the Elements (Mendeleev), including the lanthanides and actinides; examples which may be mentioned are: Sc, Y, La, Sm, Nd, Lu, Ti, Zr, Hf, Th, V, Nb, Ta and Cr. Ti, Zr and Hf are preferred.

In the formation of the metallocene structure or π complex structure, in each case a positive charge of the transition metal M is compensated by in each case a cyclopentadienyl-containing carbanion. Positive charges which still remain on the central atom M are satisfied by further, usually monovalent anions X, two identical or different anions of which can also be linked to one another (dianions,

for example monovalently or divalently negative radicals from identical or different, linear or branched, saturated or unsaturated hydrocarbons, amines, phosphines, thioalcohols, alcohols or phenols. Simple anions such as $Cr_3^-$, $NR_2^-$, $PR_2^-$, $OR^-$, $SR^-$ and the like can be bonded by saturated or unsaturated hydrocarbon or silane bridges, dianions being formed and it being possible for the number of bridge atoms to be 0, 1, 2, 3, 4, 5 or 6, 0 to 4 bridge atoms being preferred and 1 or 2 bridge atoms particularly preferred. The bridge atoms can also carry further hydrocarbon substituents R in addition to H atoms. Examples of bridges between the simple anions are, for example, 13 $CH_2$—, —$CH_2$—$CH_2$—, —$(CH_2)_3$—, $CH=CH$, —$(CH=CH)_2$—, —$CH=CH$—$CH_2$—, $CH_2$—$CH=CH$—$CH_2$—, —$Si(CH_3)_2$— and $C(CH_3)_2$—. Examples of X are: hydride, chloride, methyl, ethyl, phenyl, fluoride, bromide, iodide, the n-propyl radical, the i-propyl radical, the n-butyl radical, the amyl radical, the i-amyl radical, the hexyl radical, the i-butyl radical, the heptyl radical, the octyl radical, the nonyl radical, the decyl radical, the cetyl radical, methoxy, ethoxy, propoxy, butoxy, phenoxy, dimethylamino, diethylamino, methylethylamine, di-t-butylamino, diphenylamino, diphenylphosphino, dicyclohexylphosphino, dimethylphosphino, methylidene, ethylidene, propylidene and the ethylene glycol dianion. Examples of dianions are 1,4-diphenyl-1,3-butadienediyl, 3-methyl-1,3-pentadienediyl, 1,4-dibenzyl-1,3-butadienediyl, 2,4-hexadienediyl, 1,3-pentadienediyl, 1,4-ditolyl-1,3-butadienediyl, 1,4-bis(trimethylsilyl-1,3-butadienediyl and 1,3-butadienediyl. 1,4-Diphenyl-1,3-butadienediyl, 1,3-pentadienediyl, 1,4-dibenzyl-1,3-butadienediyl, 2,4-hexanedienediyl, 3-methyl-1,3-pentadienediyl, 1,4-ditolyl-1,3-butadienediyl and 1,4-bis(trimethylsilyl)-1,3-butadienediyl are particularly preferred. Further examples of dianions are those with heteroatoms, for example of the structure

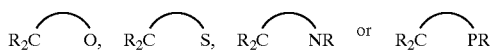

where the bridge has the meaning given. Weakly or non-coordinating anions of the abovementioned type are, moreover, particularly preferred for charge compensation.

The activation by such voluminous anions is effected, for example, by reaction of the D/A-π complex compounds, in particular the D/A-metallocenes, with tris-(pentafluorophenyl)-borane, triphenylborane, triphenylaluminum, trityl tetrakis-(pentafluorophenyl)-borate or N,N-dialkylphenylammonium tetrakis-(pentafluorophenyl)-borate or the corresponding phosphonium or sulfonium salts of borates, or alkali metal or alkaline earth metal, thallium or silver salts of borates, carboranes, tosylates, triflates, perfluorocarboxylates, such as trifluoroacetate, or the corresponding acids. D/A-metallocenes in which the anion equivalent X represents alkyl, allyl, aryl or benzyl groups are preferably employed here. Such derivatives can also be prepared "in situ" by reacting D/A metallocenes with other anion equivalents, such as X=F, Cl, Br, OR and the like, beforehand with aluminum-alkyls, organolithium compounds or Grignard compounds or zinc- or lead-alkyls. The reaction products obtainable therefrom can be activated with abovementioned boranes or borates without prior isolation.

The index n assumes the value zero, one, two, three or four, preferably zero, one or two, depending on the charge of M. The abovementioned sub-group metals can in fact assume valencies/charges of two to six, preferably two to four, depending inter alia on which of the sub-groups they belong to, in each case two of these valencies/charges being compensated by the carbanions of the metallocene compound. In the case of $La^{3+}$, the index n accordingly assumes the value one, and in the case of $Zr^{4+}$ it assumes the value two; in the case of $Sm^{2+}$, n is zero.

To prepare the metallocene compounds of the formulae (I), either in each case a compound of the above formulae (II) and (III) or in each case a compound of the above formulae (IV) and (V) or in each case a compound of the above formulae (VI) and (VII) or in each case a compound of the above formulae (VIII) and (III) or in each case a compound of the above formulae (IV) and (IX) or in each case a compound of the above formulae (X) and (VII) are reacted with one another, with elimination or splitting off of alkali metal-X, alkaline earth metal-$X_2$, silyl-X, germyl-X, stannyl-X or HX compounds, in an aprotic solvent at temperatures from −78° C. to +120° C., preferably from −40° C. to +70° C., and in a molar ratio of (II):(III) or (IV):(V) or (VI):(VII) or (VIII):(III) or (IV):(IX) or (X):(VII) of 1:0.5–2, preferably 1:0.8–1.2, particularly preferably 1:1. In the cases of reaction of (VIII) with (III) or (IV) with (IX) or (X) with (VII), it is possible to dispense with an aprotic solvent if (VIII), (IX) or (X) is liquid under the reaction conditions. Examples of such compounds eliminated or split off are: TlCl, LiCl, LiBr, LiF, LiI, NaCl, NaBr, KCl, KF, $MgCl_2$, $MgBr_2$, $CaCl_2$, $CaF_2$, trimethylchlorosilane, triethylchlorosilane, tri-(n-butyl)-chlorosilane, triphenylchlorosilane, trimethylchlorogermane, trimethylchlorostannane, dimethylamine, diethylamine, dibutylamine and other compounds which can be ascertained by the expert from the abovementioned substitution pattern.

Compounds of the formula (II) and (IV) are thus carbanions having a cyclopentadienyl skeleton or a heterocyclic skeleton which contain 1 to 3 donor groups, covalently bonded or incorporated as heterocyclic ring members and are used for the D/A bridge formation, and have a cation as a counter-ion to the negative charge of the cyclopentadienyl skeleton. Compounds of the formula (VIII) are non-charged cyclic skeletons with likewise 1 to 3 donor groups used for D/A bridge formation, but with leaving groups $E(R^1R^2R^3)$ which can easily be split off, such as silyl, germyl or stannyl groups or hydrogen, instead of the ionic groups.

The second component for formation of the metallocene compounds to be employed according to the invention, that is to say the compound of the formula (III) or (V), is likewise a carbanion having a cyclopentadienyl skeleton which is identical to the cyclopentadienyl skeleton of the compound (II) or (IV) or different from this, but carries 1 to 3 acceptor groups instead of the donor groups. In a corresponding manner, compounds of the formula (IX) are uncharged cyclopentadiene skeletons having 1 to 3 acceptor groups and likewise leaving groups $F(R^4R^5R^6)$ which can easily be split off.

In a completely analogous manner, compounds of the formulae (VI) or (X) are starting substances with a pre-formed D→A bond which are carbanion-countercation compounds or uncharged cyclopentadiene structures with a possible 1 to 3 D→A bonds in total and give the metallocene compounds (I) by reaction with compounds of the formula (VII).

The two starting substances of the preparation process, that is to say (II) and (III) or (IV) and (V) or (VI) and (VII) or (VIII) and (III) or (IV) and (IX) or (X) and (VII) react spontaneously when brought together, with simultaneous formation of the donor-acceptor group —D→A— or complexing of the metal cation M with elimination of M'X or $E(R^1R^2R^3)X$ or $F(R^4R^5R^6)X$ or HX. In the description of the donor-acceptor group, the substituents on D and A have been omitted for clarity.

M' is one cation equivalent of an alkali metal or alkaline earth metal, such as Li, Na, K, ½Mg, ½Ca, ½Sr, ½Ba or thallium.

The compounds of the formula (XIIIa+b) are prepared analogously in the above-mentioned manner.

Solvents for the preparation process are aprotic, polar or non-polar solvents, such as aliphatic and aromatic hydrocarbons or aliphatic and aromatic halogeno-hydrocarbons. Other aprotic solvents such as are known to the expert are also possible in principle, but because of the easier working up, those with boiling points which are too high are less preferred. Typical examples are: n-hexane. cyclohexane, pentane, heptane, petroleum ether, toluene, benzene, chlorobenzene, methylene chloride, diethyl ether, tetrahydrofuran and ethylene glycol dimethyl ether.

The starting substances of the formulae (II), (III), (IV) and (V) can be prepared by processes known from the literature or analogously to these. Thus, for example, trimethylsilyl-cyclopentadiene, which is available on the market, can be reacted first with butyl-lithium and then with trimethylsilyl chloride to give bis(trimethylsilyl)-cyclopentadiene analogously to J. of Organometallic Chem. (1971), 29, 227. This product can in turn be reacted with boron trichloride to give trimethylsilyl-cyclopentadienyl-dichloroborane (analogously to J. of Organometallic Chem. (1979), 169, 327), which finally can be reacted with titanium tetrachloride analogously to J. of Organometallic Chem. (1979), 169, 373 to give dichloroboryl-cyclopentadienyl-titanium trichloride. This compound mentioned last is already a prototype of the compounds of the formula (III); the compound mentioned last can furthermore be reacted selectively with trimethylaluminum, the two chlorine atoms bonded to the boron atom being replaced by methyl groups, a further compound of the formula (III) being demonstrated. Cyclopentadienyl-thallium, which is available on the market, can be reacted with chloro-diphenylphosphine and further with butyl-lithium analogously to the process description in J. Am. Chem. Soc. (1983) 105, 3882 and Organometallics (1982) 1, 1591, a prototype of compounds of the formula (II) being obtained. The formation of dimethylstannyl-diphenylphosphine-indene by reaction of indene first with butyl-lithium, as already mentioned above, and then with chlorodiphenylphosphine may be mentioned as a further example; further reaction, first again with butyl-lithium and then with chloro-tributyltin, gives the compound mentioned, which, after further reaction with zirconium tetrachloride, gives diphenylphosphino-indenyl-zirconium trichloride as a representative of compounds of the formula (IV). Such syntheses and preparation procedures are familiar to the expert operating in the field of organo-metallic and organoelemental chemistry and are published in numerous literature references, of which only a few are given by way of example above.

The examples described below show how such heterocyclic precursors and catalysts according to the invention are accessible. Thus, pyrrolyl-lithium (formula II) can be prepared from pyrrole by reaction with butyl-lithium, as described, for example, in J. Amer. Chem. Soc. (1982), 104, 2031. Trimethylstannyl-phosphol (formula VIII) is obtained by reaction of 1-phenylphosphol with lithium, followed by aluminum trichloride, phospholyl-lithium (formula II) being formed, which in turn further reacts with trimethylchlo-rostannane to give trimethylstannyl-phosphol. Cf.: J. Chem. Soc. Chem. Comm. (1988), 770. This compound can be reacted with titanium tetrachloride to give phospholyl-titanium trichloride (formula IV).

The metallocene compounds to be employed according to the invention are out-standingly suitable as catalysts in processes for the homo- and copolymerization of one or more optionally substituted α-olefins in the gas, solution, high pressure or slurry phase at −60 to +250° C., preferably 0 to 200° C., under a pressure of 0.5 to 5000 bar, preferably 1 to 3000 bar, it being possible to carry out the reaction in the presence or absence of saturated or aromatic hydrocarbons or of saturated or aromatic halogeno-hydrocarbons. Such polymerizations can be carried out discontinuously or, preferably, continuously. They can also be carried out by the semibatch process. Such processes can also be carried out in more than one reactor or reaction zone. In the case of a plurality of reaction zones, the polymerization can be carried out under different polymerization conditions. Thus, a prepolymer which is particularly suitable as a heterogeneous catalyst for the actual (co)polymerization in further reactors can be formed in one reactor. Heterogeneous D/A catalysts on inorganic supports are particularly suitable for the formation of such prepolymers. $10^1$ to $10^{12}$ mol of (co) monomers are reacted per mole of π complex compounds or metallocene compounds. The π complex compounds or metallocene compounds can be employed together with cocatalysts. The ratio of the amounts between the π complex compounds or metallocene compound and cocatalyst is 1 to 100,000 mol of cocatalyst per mole of π complex compound or metallocene. Cocatalysts are understood as meaning, for example, aluminoxane compounds such as those of the formula

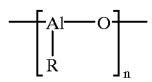

(XII)

in which
R represents $C_1$–$C_{20}$-alkyl, $C_6$–$C_{12}$-aryl or benzyl and
n denotes a number from 2 to 50, preferably 10 to 35.

It is also possible to employ a mixture of various aluminoxanes or a mixture of precursors thereof (aluminum-alkyls) in combination with water (in gaseous, liquid, solid or bonded form, for example as water of crystallization). The water can also be fed in as (residual) moisture of the polymerization medium, of the monomer or of a support, such as silica gel.

The bonds projecting from the square brackets of formula (XI) contain R groups or $AlR_2$ groups as end groups of the oligomeric aluminoxane. Such aluminoxanes are as a rule present as a mixture of a plurality of them of different chain lengths. Fine analysis has also shown aluminoxanes with a cyclic or cage-like structure. Aluminoxanes are compounds which are available on the market. In the specific case of R=$CH_3$, methylaluminoxanes (MAO) are referred to.

Further cocatalysts are aluminum-alkyls, lithium-alkyls or organo-Mg compounds, such as Grignard compounds, or partly hydrolyzed organoboron compounds. Preferred cocatalysts are aluminoxanes.

The activation with the cocatalysts or the production of the voluminous non- or weakly coordinating anions can be carried out in an autoclave or in a separate reaction vessel (preforming). The activation can be carried out in the presence or absence of the monomer(s) to be polymerized. The activation can be carried out in an aliphatic or aromatic or halogenated solvent or suspending agent.

The π complex compounds or the metallocene compounds and the aluminoxanes can be employed both as such in homogeneous form and individually or together in heterogeneous form on supports. The support material here can be inorganic or organic in nature, such as silica gel, $Al_2O_3$, $MgCl_2$, NaCl, cellulose derivatives, starch and polymers, such as polyethylene or polypropylene. It is equally possible here to apply the π complex compound or the metallocene compound first or to apply the aluminoxane first, to the support, and then to add the other particular component. Equally, however, the it complex compound or the metallocene compound can also be activated in homogeneous or heterogeneous form with the aluminoxane and the activated metallocene compound can then be applied to the optionally aluminoxane-charged support.

Support materials are preferably treated by heat and/or chemicals in order to adjust the water content or the OH group concentration to a defined value or to keep it as low as possible. A chemical pretreatment can comprise, for example, reaction of the support with aluminum-alkyl. Inorganic supports are usually heated at 100° C. to 1000° C. for 1 to 100 hours before use. The surface area of such inorganic supports, in particular of silica ($SiO_2$), is between 10 and 1000 m²/g, preferably between 100 and 800 m²/g. The particle diameter is between 0.1 and 500 micrometers ($\mu$), preferably between 10 and 200 $\mu$.

Olefins which are to be reacted by homo- or copolymerization are, for example, ethylene, propylene, but-1-ene, pent-1-ene, hex-1-ene, oct-1-ene, 3-methyl-but-1-ene, 4-methyl-pent-1-ene, 4-methyl-hex-1-ene and iso-octene.

Such olefins can furthermore be substituted, for example by phenyl, substituted phenyl, halogen, the esterified carboxyl group or the acid anhydride group; compounds of this type are, for example, styrene, methylstyrene, chlorostyrene, fluorostyrene, 4-vinyl-biphenyl, vinyl-fluorene, vinyl-anthracene, methyl methacrylate, ethyl acrylate, vinylsilane, trimethyl-allylsilane, vinyl chloride, vinylidene chloride, tetrafluoroethylene, vinylcarbazole, vinylpyrrolidone, vinyl ethers and vinyl esters. Ring-opening polyadditions, for example of lactones, such as ε-caprolactone or δ-valerolactone, or of lactarns, such as ε-caprolactam, are furthermore possible according to the invention. Preferred monomers are: ethylene, propylene, butene, hexene, octene and methyl methacrylate.

The homo- or copolymerizations or polyadditions to be carried out using the π complex compounds or metallocene compounds according to the invention are carried out adiabatically or isothermally. These are high pressure processes in autoclaves or tube reactors, solution processes and also polymerization in bulk, processes in the slurry phase in stirred reactors or loop reactors, and processes in the gas phase, the pressures for the slurry, solution and gas phase not exceeding 65 bar. All these processes have been known for a long time and are familiar to the expert. It is an advantage of the π complex compounds and metallocene compounds according to the invention that, by choice of the substituents, they can be prepared both as soluble π complex compounds or metallocene compounds optionally applied to supports and as insoluble π complex compounds or metallocene compounds. Soluble π complex compounds and metallocene compounds are employed for the high pressure process and the solution process; heterogeneous metallocene compounds are employed in the slurry phase and the gas phase.

(Co)polymers which can be prepared according to the invention are distinguished by a high crystallinity and optimized melting range. This is achieved by a low degree of branching in the case of polyethylene and by a high tacticity (isotactic or syndiotactic) in the case of polymers of olefins having 3 or more C atoms. Copolymers are distinguished by a high regularity in the incorporation of the comonomers. Examples of such polymers are high-density linear polyethylene (HDPE), isotactic polypropylene (iPP), syndiotactic polypropylene (sPP), i- or s-polybutene or -polyhexene, polyoctene, linear low-density copolymers, for example ethylene with $C_3$–$C_8$-α-olefin (linear low density polyethylene LLDPE), that is to say ethylene/propylene, ethylene/butylene, ethylene/hexene and ethylene/octene and furthermore, for example, propylene/butylene, propylene/hexene and others. HDPE, LLDPE with butylene, hexene or octene as comonomers, iPP and sPP are preferred.

The π complex compounds to be employed according to the invention, in particular the metallocene compounds, allow a defined opening of the two cyclopentadienyl skeletons like a beak due to the donor-acceptor bridge, a controlled selectivity, a controlled molecular weight distribution and a uniform incorporation of (co)monomers being ensured, in addition to a high activity. As a result of a defined beak-like opening, there is also space for voluminous (co) monomers. A high uniformity in the molecular weight distribution furthermore results from the uniform and defined site of the polymerization taking place by insertion (single site catalyst).

The molecular weight distribution can be modified (broadened) in a controlled manner by employing a plurality of D/A catalysts simultaneously, in order to establish a certain profile of properties of the material. Accordingly, it is also possible to employ one or more D/A catalysts in combination with other metallocenes which have no D/A bridge.

The D/A structure can have the effect of extra-stabilizing the catalysts up to high temperatures, so that the catalysts can also be employed in the high temperature range. The possible thermal dissociation of the donor-acceptor bond is reversible and, as a result of this self-organization process and self-repair mechanism, leads to particularly high-quality catalyst properties. The D/A metallocene structures according to the invention allow, for example, a degree of defect-free polyethylene formation which cannot be achieved with conventional catalysts. Correspondingly, the ethene polymers can have exceptionally high melting points, for example above 135° C. to 160° C. (maximum of the DSC curve). Linear polyethylenes which are obtained directly in the polymerization process preferably include those which have melting points of 140 to 160° C. (maxima of the DSC curves), preferably 142 to 160° C., particularly preferably 144 to 160° C., especially preferably 146 to 160° C. This applies in particular to those which can be prepared with the metallocene compounds claimed. Compared with the known polyethylenes, such novel high-melting polyethylenes show, for example, improved mechanical properties and heat distortion performance (sterilizability for medical applications) and as a result open up possibilities of use which did not hitherto seem possible for polyethylene and, for example, would hitherto be met only by highly tactic polypropylene. Further features are high melting enthalpies and high PE molecular weights.

Within a wide temperature range, the PE molecular weight is reduced by increasing the polymerization temperature without a noticeable reduction in activity and without leaving overall the range of industrially advantageous high PE molecular weights and high PE melting points.

For the preparation of isotactic polyolefins, for example, quasi-rac-bis(indenyl)metallocenes with a D/A bridge, which can additionally carry, for example, alkyl, aryl and/or silyl substituents or benzo-fused structures, for example in position 2 or in position 4, 5, 6 or 7, to increase the molecular weight and isotacticity and melting point, are particularly suitable. However, D/A-bis(cyclopentadienyl)-metallocenes with (3,3') substitution patterns of comparable symmetry are also possible.

D/A-bridged (cyclopentadienyl)(fluorenyl)-metallocenes or (cyclopentadienyl)(3,4-disubstituted cyclopentadienyl)-metallocenes are correspondingly suitable, for example, for the preparation of syndiotactic polyolefins.

It has furthermore been found that metallocene compounds and π complex compounds of suitable symmetry which are to be employed according to the invention have the effect of a stereospecific (isotactic, syndiotactic) polymerization on α-olefins from 3 C atoms, but induce an increasingly non-specific (atactic) linkage of the monomer units on the same monomer in the upper part of the temperature range mentioned. This phenomenon has not yet been investigated completely, but could coincide with the observation that coordinate bonds which are overlapped by an ionic bond, such as the donor-acceptor bonds in the metallocene compounds according to the invention, show an increasing reversibility at a higher temperature. It has furthermore been found, for example in the case of ethylene-propylene copolymerization, that if the same amount of the two comonomers is available, a highly propylene-containing copolymer is formed at a low copolymerization temperature, while as the polymerization temperature increases, the propylene content decreases, until finally predominantly ethylene-containing polymers (LLDPE) are formed at a high temperature. The reversible dissociation and association of the D/A structure and the rotation of the π skeletons against one another which becomes possible as a result can be shown schematically as follows:

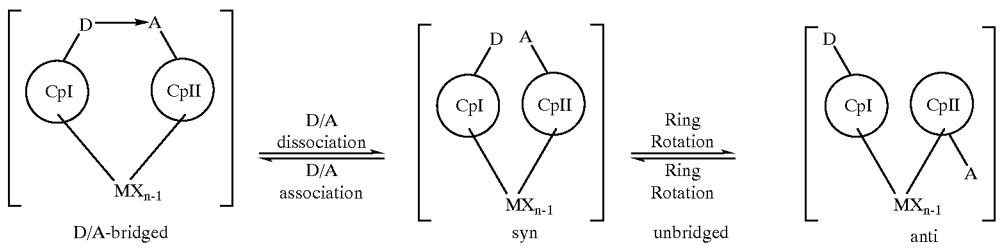

and

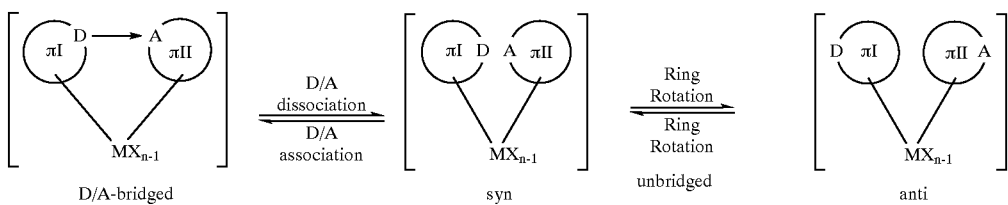

Another valuable property of the D/A-π complex compounds, for example D/A-metallocene compounds, according to the invention is the possibility of self-activation and therefore of dispensing with expensive catalysts, in particular in the case of dianionic

derivatives.

In this case, the acceptor atom A bonds an X ligand in the open form of the D/A-π complex compounds, for example D/A-metallocene compound, for example one side of a dianion, to form a zwitterionic metallocene structure, and thus generates a positive charge in the transition metal, while the acceptor atom A assumes a negative charge. Such a self-activation can be intramolecular or intermolecular.

This may be illustrated by the example of the preferred linkage of two X ligands to a chelate ligand, that is to say of the butadienediyl derivative:

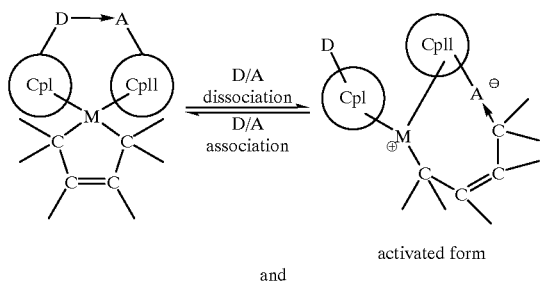

-continued

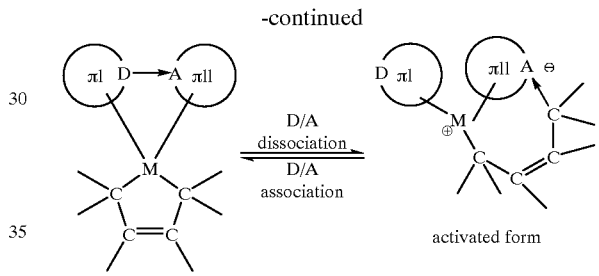

The bonding site between the transition metal M and H or substituted or unsubstituted C, in the formula example substituted C of the butadienediyl dianion shown, is then the site of olefin insertion for the polymerization.

EXAMPLES

All the reactions were carried out under strictly anaerobic conditions using Schlenk techniques or the high vacuum technique. The solvents used were dry and saturated with argon. Chemical shifts δ are stated in ppm, relative to the particular standard: $^1$H(tetramethylsilane), $^{13}$C (tetramethylsilane), $^{31}$P(85% strength $H_3PO_4$), $^{11}$B(boron trifluoride-etherate-18.1 ppm). Negative signs denote a shift to a higher field.

Example 1

(Bis-(trimethylsilyl)-cyclopentadiene, compound 1)

14.7 g (0.106 mol) of trimethylsilyl-cyclopentadiene (obtained from Fluka) and 150 ml of tetrahydrofuran (THF) were introduced into a reaction flask and cooled to 0° C. 47.4 ml of a solution of butyl-lithium in n-hexane (2.3 molar; total amount 0.109 mol) were added dropwise in the course of 20 minutes. When the addition was complete, the yellow solution was stirred for a further hour; thereafter, the cooling bath was removed. The solution was stirred for a further hour at room temperature and then cooled to −20° C. 14.8 ml (0.117 mol) of trimethylsilyl chloride were then added dropwise in the course of 10 minutes and the reaction mixture was stirred at −10° C. for 2 hours. Thereafter, the cooling bath was removed and the reaction solution was warmed to room temperature and subsequently stirred for a further hour. The reaction mixture was filtered through Celite; the filter was washed with hexane and the hexane was removed from the combined filtrate in vacuo. On distillation at 26° C. under 0.4 mbar, the crude product gave 19 g of pure product of the compound 1 (85% of the theoretical yield). The boiling point and NMR data correspond to the literature data (J. Organometallic Chem. 29 (1971), 227; ibid. 30 (1971), C 57; J. Am. Chem. Soc. 102, (1980), 4429; J. Gen. Chem. USSR, English translation 43 (1973), 1970; J. Chem. Soc., Dalton Trans. 1980, 1156)

$^1$H-NMR (400 MHz, $C_6D_6$): δ=6.74 (m, 2H), 6.43 (m, 2H), −0.04 (s, 18H).

Example 2

(Trimethylsilyl-cyclopentadienyl-dichloroborane, compound 2)

16 g (0.076 mol) of the compound 1 were introduced into a round-bottomed flask equipped with a dry ice cooling bath. 8.9 g (0.076 mol) of $BCl_3$ were condensed at −78° C. in a Schlenk tube and then added dropwise to the round-bottomed flask over a period of 5 minutes. The reaction mixture was warmed slowly to room temperature in the course of 1 hour and then kept at 55 to 60° C. for a further 2 hours. All the volatile compounds were removed in vacuo (3 mm Hg=4 mbar). Subsequent distillation at 39° C. under 0.012 mbar gave 14.1 g of the compound 2 (85% of the theoretical yield). The $^1$H-NMR agreed with the literature data and showed that a number of isomers had been prepared (cf. J. Organometallic Chem. 169 (1979), 327). $^1$B-NMR (64.2 MHz, $C_6D_6$): δ=+31.5.

Example 3

(Dichloroboranyl-cyclopentadienyl-titanium trichloride, compound 3)

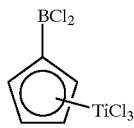

3

11.4 g (0.052 mol) of the compound 2 and 100 ml of methylene chloride ($CH_2Cl_2$) were introduced into a 250 ml Schlenk tube. This solution was cooled to −78° C., and 9.8 g (5.6 ml, 0.052 mol) of titanium tetrachloride were added dropwise in the course of 10 minutes. The resulting red solution was warmed slowly to room temperature and stirred for a further 3 hours. The solvent was removed in vacuo and a dirty yellow product was obtained. 200 ml of hexane were added to the crude solid and the resulting yellow solution was filtered and cooled overnight in a refrigerator, 12.3 g (79% of the theoretical yield) of yellow crystals of the compound 3 being obtained. It should be pointed out that in J. Organometallic Chem. 169 (1979), 373, 62% of the theoretical yield was obtained, the reaction being carried out in a hydrocarbon solvent, such as petroleum ether or methylcyclohexane.

$^1$H-NMR (400 MHz, $CD_2Cl_2$): δ=7.53 (t, J=2.6 Hz, 2 H), 7.22 (t, J=2.6 Hz, 2H). $^{11}$B-NMR (64.2 MHz, $CD_2Cl_2$): δ=+33.

Example 4

(Dimethylboranyl-cyclopentadienyl-titanium trichloride, compound 4)

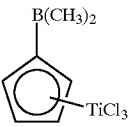

4

2.37 g (0.0079 mol) of the compound 3 were dissolved in 100 ml of hexane in a round-bottomed flask. This solution was cooled to 0° C. and 4 ml of a 2 molar solution of aluminum-trimethyl in toluene (0.008 mol) were added dropwise. When the addition was complete, the cooling bath was removed and all the volatile compounds were removed in vacuo. The yellow solid which remained was now dissolved in pentane, solid contents were filtered off and the clear filtrate was cooled to −78° C., 1.5 g (74% of the theoretical yield) of compound 4 being obtained. It should be noted that in J. Organometallic Chem. 169 (1979), 373 a yield of 87% of the theoretical yield is stated, tetramethyltin being used as the alkylating agent; however, it was not possible to obtain the compound 4 in a form free from the trimethyltin chloride formed.

$^1$H-NMR (400 MHz, $CD_2Cl_2$): δ=7.48 (t, J=2.5 Hz, 2H), 7.23 (t, J=2.5 Hz, 2H), 1.17 (s, 6H). $^{11}$B-NMR (64.2 MHz, $CD_2Cl_2$): δ=+56.

Example 5

(Diphenylphosphine-cyclopentadienyl)-lithium, compound 6)

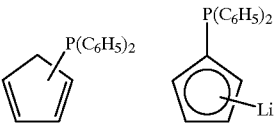

50 g (0.186 mol) of cyclopentadienyl-thallium (obtained from Fluka) were introduced together with 300 ml of diethyl ether into a 500 ml flask. The suspension was cooled to 0° C. and 34.2 ml (0.186 mol) of diphenylchlorophosphine were added dropwise in the course of 10 minutes. The suspension was then warmed to room temperature and stirred for one hour, and finally filtered through a frit. The solvent was then stripped off in vacuo and left behind 39.5 g (85% of the theoretical yield) of the intermediate product diphenylphosphino-cyclopentadiene, compound 5. A content of 18.6 g (0.074 mol) of the compound 5 was then diluted with toluene and cooled to 0° C. 33.2 ml of a 2.24 molar solution of butyllithium in hexane (0.074 mol) were added to this solution in the course of 10 minutes. After warning to room temperature and after stirring for 2 hours, the yellow solution gave a precipitate, which was filtered off and washed with toluene and then with hexane. After drying in vacuo, 13.2 g of the compound 6 (70% of the theoretical yield) were obtained as a brownish powder (cf. J. Am. Chem. Soc. 105 (1983), 3882; Organometallics 1 (1982), 1591).

$^1$H-NMR (400 MHz, $d_8$TBF): δ=7.3 (m, 4H), 7.15 (m, 6H), 5.96 (m, 2H), 5.92 (m, 2H), $^{31}$P-NMR (161.9 MHz, $d_8$THF): δ=−20.

Example 6

((C$_6$H$_5$)$_2$P B(CH$_3$)$_2$-bridged bis-(cyclopentadienyl)-titanium dichloride, compound 7)

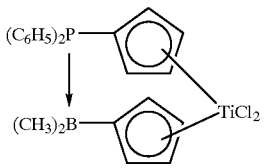

0.36 g (0.00139 mol) of the compound 6 and 20 ml of toluene were introduced into a round-bottomed flask. The solution formed was cooled to −20° C. and a solution of 0.36 g (0.00139 mol) of the compound 4 in 20 ml of toluene was added dropwise in the course of 20 minutes. When the dropwise addition had ended, the solution was heated to room temperature in the course of 2 hours and stirred at this temperature for an additional hour. Undissolved material was removed over a frit and the solvent was distilled off in vacuo. The red oily solid was then washed with hexane, which was decanted off, and the solid was dried again in vacuo. 0.28 g (42% of the theoretical yield) of the compound 7 was obtained as a red powder by this procedure.

$^1$H-NMR (300 MHz, CD$_2$Cl$_2$): δ=7.6–7.3 (br, m, 10H), 6.92 (m, 2H), 6.77 (m, 4H), 6.60 (m, 2H), 0.29 (d, J$_{PH}$=19 Hz, 6H); $^{31}$P-NMR (161.9 MHz, CD$_2$C$_2$):=17.1 (br); $^{11}$B-NMR (64.2 MHz, CD$_2$Cl$_2$): δ=−29 (br).

Example 7

(Tributylstannyl-diphenylphosphino-indene, compound 8)

10 g (0.086 mol) of indene were introduced into a round-bottomed flask, diluted with 200 ml of diethyl ether and cooled to −20° C. 36 ml of a 2.36 molar solution of butyl-lithium (0.085 mol) in n-hexane were added to this solution, the solution immediately assuming a yellow color. The cooling bath was removed and the reaction mixture was allowed to warm to room temperature and was stirred for a further hour. Thereafter, the reaction mixture was cooled again to 0° C. and 19 g (15.9 ml, 0.086 mol) of diphenylchlorophosphine were added, a precipitate being formed. The cooling bath was removed again and the solution was allowed to warm to room temperature while being subsequently stirred for a further hour. The solution was then cooled again to −20° C. and 36 ml (0.085 mol) of butyl-lithium in n-hexane were added dropwise. When the addition had ended, the cooling bath was removed again and the temperature rose to room temperature; the solution was subsequently stirred for a further 1.5 hours. The suspension was then cooled again to 0° C. and 28 g (0.086 mol) of tributyltin chloride were added dropwise. The resulting suspension was warmed to room temperature and stirred for a further 1.5 hours and subsequently filtered through a frit, and the solvent was removed in vacuo. 46.9 g of the compound 8 (92% of the theoretical yield) remained as a heavy yellow oil.

$^1$H-NMR (400 MHz, CDCl$_3$): δ=7.5–7.3 (m, 6H), 7.28 (brs, 6H), 7.14 (pseudo-d t, 7.3 Hz/1.0 Hz, 1H), 7.08 (t, J=7.3 Hz, 1H), 6.5 (br m, 1H), 4.24 (br s, 1H), 1.4–1.25 (m, 6H), 1.25–1.15 (m, 6H), 0.82 (t, J=7.2 Hz, 9H), 0.53 (t, J=8 Hz, 6H), $^{31}$P-NMR (161.9 MHz, CDCl$_3$): δ=−20.6.

Example 8

(Diphenylphosphino-indenyl-zirconium trichloride, compound 9)

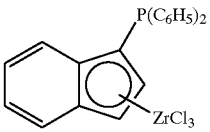

A solution of 37 g (0.0628 mol) of the compound 8 in 300 ml of toluene was added to a suspension of 14.6 g of ZrCl$_4$ (99.9% pure, 0.0628 mol, obtained from Aldrich) in 100 ml of toluene at room temperature in the course of 3 hours. The solution immediately became red and slowly changed into orange and finally into yellow. After subsequently stirring for 4 hours, the yellow precipitate was filtered off and washed with toluene and then with hexane. The solid was dried in vacuo and gave 15.3 g (50% of the theoretical yield) of the compound 9 as a free-flowing yellow powder. The yield could easily be increased to more than 70% by carrying out the reaction at a lower temperature, for example 30 minutes at −30° C. and 5 hours at 0° C. The product could be purified further by washing out residual tin compound using pentane in a Soxhlet extractor (extraction time: 8 hours).

Example 9

((C$_6$H$_5$)$_2$P BCl$_2$-bridged indenyl-cyclopentadienylzirconium dichloride, compound 10)

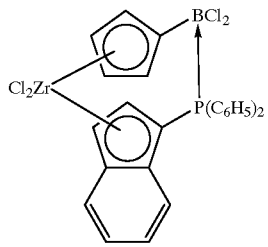

4.43 g (0.0089 mol) of the purified compound 9 and 100 ml of toluene were introduced into a Schlenk tube. 1.95 g (0.0089 mol) of the compound 2 were added to this suspension. The yellow suspension was stirred at room temperature for 6 hours; during this period, a pale white precipitate formed. This precipitate (4.1 g, 75% of the theoretical yield) was isolated by filtration and found to be essentially pure material.

$^1$H-NMR (500 MHz, CD$_2$Cl$_2$): δ=7.86 (pseudo ddd, J=8.5/2.5/1 Hz, 1H), 7.75–7.55 (m, 10H), 7.35 (pseudo ddd, J=8.5/6.9/0.9 Hz, 1H), 7.32 (br t, J=3.1 Hz, 1H), 7.22 (pseudo ddd, J=8.8/6.8/1.1 Hz, 1H), 7.06 (pseudo ddd, J=3.4/3.4/0.8 Hz, 1H), 6.92 (m, 1H), 6.72 (m, 1H), 6.70 (br m, 1H), 6.61 (pseudo q, J=2.3 Hz, 1 H), 6.53 (br d, 8.7 Hz, 1H); $^{31}$P-NMR (161.9 MHz CD$_2$Cl$_2$):=6.2 (br, m); $^{11}$B-NMR (64.2 Mz, CD$_2$Cl$_2$): δ=−18 (br).

Example 10

(($(C_6H_5)_2P$  $B(CH_3)_2$-bridged  indenyl-cyclopentadienylzirconium dichloride, compound 11)

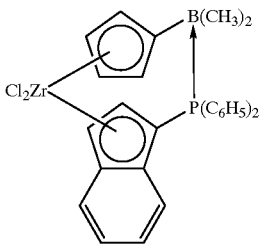

50 ml of toluene were added to 1.5 g (0.00247 mol) of compound 10 from Example 9. The suspension was cooled to 0° C. and 1.2 ml of a 2 molar solution of trimethylaluminum in hexane (0.0024 mol) were added dropwise in the course of 5 minutes. When the addition was complete, the cooling bath was removed and the solution was allowed to warm up to room temperature and was further stirred for 2 hours. The remaining precipitate was filtered off and the solvent was stripped off from the filtrate in vacuo, 0.37 g (26% of the theoretical yield) of the compound 11 remaining as a brownish solid.

$^{31}$P-NMR (161.9 MHz, $CD_2Cl_2$): δ=14.6; $^1$B-NMR (64.2 MHz, $CD_2Cl_2$):=−28

Example 11
(Trimethylsilyl-indene, compound 12)

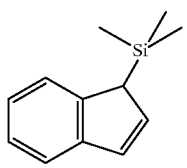

25 ml of indene (0.213 mol, distilled over $CaH_2$ in vacuo) were introduced into a round-bottomed flask which contained 100 ml of THF and was cooled to 0° C. 94 ml of a 2.3 molar solution of butyl-lithium in hexane (0.216 mol) were added in the course of 20 minutes. When the addition was complete, the mixture was stirred for 20 minutes and then warmed to room temperature and stirred for a further 30 minutes. After cooling to −20° C., 27.5 ml (0.216 mol) of trimethylchlorosilane were added dropwise, a slightly cloudy orange-colored solution being formed. After stirring at −10° C. for 1 hour and at 0° C. for 1.5 hours, the solution was warmed to room temperature and the solvent was removed in vacuo. After dissolving again in hexane, LiCl was filtered off and the hexane was removed in vacuo. Distillation of the product (0.045 mbar, 58 to 60° C.) gave 26.6 g (66% of the theoretical yield) of 12.

$^1$H-NMR (400 MHz, $CDCl_3$): δ=7.49 (t, J=7.6 Hz, 1 H), 7.28 (ddd, J=7.3/7.2/1 Hz, 1 H), 7.21 (ddd, J=7.3/7.3/1.1 Hz, 1 H), 6.96 (dd, J=5.6/1.2 Hz, 1 H), 6.69 (dd, J=5.3/1.8 Hz, 1 H), 3.56 (s, 1 H), 0.0 (s, 9 H).

Example 12
(Bis-(trimethylsilyl)-indene, compound 13)

25.4 g (0.135 mol) of the compound 12 were introduced into a round-bottomed flask which contained 100 ml of THF and was cooled to 0° C. 59 ml of a 2.3 molar solution of butyl-lithium in hexane (0.136 mol) were added in the course of 20 minutes. When the addition was complete, the mixture was stirred for 20 minutes and then warmed to room temperature. After stirring for 30 minutes, it was cooled to −20° C. and 17.3 ml of trimethylchlorosilane (0.136 mol) were added dropwise, a slightly cloudy orange-colored solution being formed. The solution was stirred at 0° C. for 1 hour and at room temperature for 1 hour and the solvent was then removed in vacuo. After redissolving in hexane, LiCl was filtered off and the hexane was removed in vacuo. 32 g (90% of the theoretical yield) of 13 were obtained as an oil. Cf. J. Organometal. Chem. 23 (1970), 407; hexane there instead of THF.

$^1$H-NMR (400 MHz, $CDCl_3$): δ=7.62 (d, J=7.6 Hz, 1 H), 7.52 (d, J=7.5 Hz, 1 H), 7.23 (ddd, J=7.35/7.3/0.9 Hz, 1 H), 6.9 (d, J=1.7 Hz, 1 H), 3.67 (d, J=1.6 Hz, 1 H), 0.38 (s, 9 H), 0.0 (s, 9 H).

Example 13

(Trimethylsilyl-dichloroboranyl-indene, compound 14)

In a manner similar to the preparation of compound 2, 12.3 g (0.047 mol) of compound 13 were introduced into a round-bottomed flask which was cooled to −30° C. and had a reflux condenser cooled with dry ice. 5.6 g (0.046 mol) of $BCl_3$ were added to this. When the addition was complete, the cooling bath was removed and the reaction mixture warmed to room temperature and was stirred for 3 hours. The temperature was then raised to 55° C. for 6 hours. After cooling and removal of the volatile contents in vacuo, the crude product was obtained. Distillation under a high vacuum gave the purified product, the main isomer of which was identified as follows:

$^1$H-NMR (200 MHz, $CDCl_3$): δ=8.3 (d, J=7 Hz, 1 H), 8.1 (d, J=1.8 Hz, 1 H), 7.5 (dd, J=7.0/1.2 Hz, 1 H), 7.4 (m, 3 H), 4.0 (d, J=1.8 Hz, 1 H), 0.1 (s, 9 H); $^{11}$B-NMR (64.2 MHz, $CD_2Cl_2$): δ=38 (br).

Example 14

(($(C_6H_5)_2P$-$BCl_2$-bridged bis-(indenyl)-zirconium dichloride, compound 15)

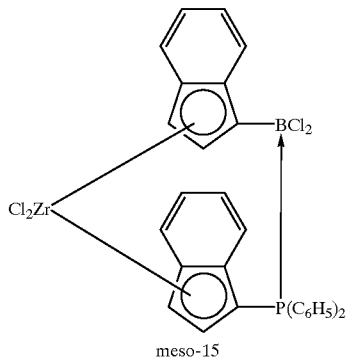

meso-15

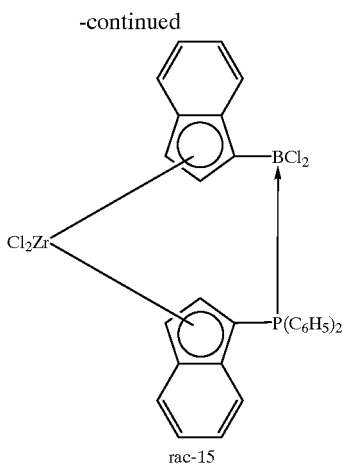

rac-15

4.5 g of the compound 14 (0.017 mol) were added to a suspension of 8.3 g of compound 9 (0.017 mol) into 200 ml of toluene; the mixture was heated to 50° C. and stirred for 5 hours. After cooling and filtration, 200 ml of hexane were added, after which a precipitate precipitated out of the clear yellow solution and was filtered off and dried in vacuo. The product was identified as the meso-isomer of 15 according to its X-ray analysis. The P→B bond length of the bridge was determined as 2.01 Å. A second precipitate, which was determined as the racemic isomer of 15, was obtained by concentration of the toluene/hexane solution to about 10 ml and further addition of 200 ml of hexane.

Example 15
(N,N-Dimethyl-O-(methylsulfonyl)-hydroxylamine, compound 16)

9.0 g of N,N-dimethyl-O-hydroxylamine hydrochloride (0.092 mol) were suspended in 70 ml of $CH_2Cl_2$ which contained 20 g of triethylamine (0.2 mol), and the suspension was cooled to −10° C. 9.5 g of methylsulfonyl chloride (0.083 mol), dissolved in 70 ml of $CH_2Cl_2$, were slowly added dropwise to the cooled suspension. When the addition was complete, the mixture was subsequently stirred for 1 hour. Thereafter, ice-water was added to the reaction mixture and the organic phase was separated off. The water which remained was washed with ether. The wash ether and the $CH_2Cl_2$ fraction were combined and dried over $Na_2SO_4$ and the solvents were removed in vacuo at −10° C. 5.9 g (46% of the theoretical yield) of compound 16 remained as an oil, which was stored at −20° C. Cf. Angew. Chem. International Edition English 17 (1978), 687.

$^1$H-NMR (400 MHz, CDCl$_3$): δ=3.03 (s, 3H), 2.84 (s, 6H).

Example 16
(N,N-Dimethylamino-cyclopentadienyl-lithium, compound 17)

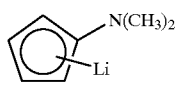

A solution of 3 g of cyclopentadienyl-lithium (0.042 mol) in 30 ml of THF was slowly added to a solution of 5.9 g of the compound 16 (0.042 mol) in 20 ml of THF at −30° C. The mixture was then warmed to −20° C. and stirred for 30 minutes. Hexane was then added and the solution was filtered. Thereafter, 1.8 ml of a 2.3 molar solution of butyl-lithium (0.042 mol) in hexane were added at −20° C., whereupon a precipitate formed. The precipitate was filtered off and washed twice with 20 ml of hexane each time. After drying in vacuo, 2.0 g (40% of the theoretical yield) of the compound 17 were obtained as a white powder. Cf. Angew. Chem. International Edition English 19 (1980), 1010.

$^1$H-NMR (400 MHz, THF): δ=5.34 (br d, J=2.2 Hz, 2H), 5.15 (br d, J=2.2 Hz, 2H), 2.56 (s, 6H).

Example 17
(($(CH_3)_2$N-B($CH_3$)$_2$-bridged bis-(cyclopentadienyl)-titanium dichloride, compound 18)

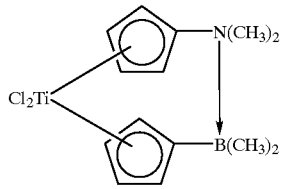

A solution of 0.18 g of the compound 4 (0.7 mmol) in 10 ml of toluene was added to a suspension of 0.081 g of the compound 17 (0.7 mmol) in 10 ml of toluene at −20° C. in the course of 10 minutes, a deep red solution being formed. After warming at room temperature for 2 hours, the solution was filtered and the solvent was removed in vacuo. After the red powder formed had been redissolved in 10 ml of warm toluene and insoluble material had been filtered off, the solution was stored overnight in a refrigerator, 0.1 g (43% of the theoretical yield) being formed as red needles.

$^1$H-NMR (400 MHz, CD$_2$Cl$_2$): δ=6.85 (t, J=2.3 Hz, 2H), 6.15 (t, J=2.3 Hz, 2H), 6.1 (t, J=2.8 Hz, 2H), 5.57 (t, J=2.8 Hz, 2H), 1.98 (s, 6H), 0.35 (s, 6H); $^{11}$B-NNR (64.2 MHz, CD$_2$Cl$_2$): δ=2.8 (br).

Example 18
(Tributylstannyl-diisopropylphosphine-indene, compound 19)

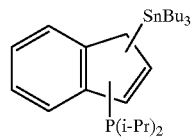

100 ml of ether were introduced into a round-bottomed flask which contained 3.8 g (0.033 mol) of indene; the mixture was cooled to −20° C. 14.4 ml of a 2.3 molar solution of butyl-lithium in hexane (0.033 mol) were added to this solution in the course of 5 minutes, a yellow solution being formed. After removal of the cooling bath, the solution was warmed to room temperature and subsequently stirred for 1.5 hours. Thereafter, the reaction mixture was cooled to 0° C. and 5.0 g of chlorodiisopropylphosphine (0.033 mol) were added, whereupon a precipitate formed. After removal of the cooling bath, the solution was warmed to room temperature and stirred for 1 hour. Thereafter, the solution was cooled to −20° C. and 14.4 ml of a 2.3 molar solution of butyl-lithium in hexane (0.033 mol) were added dropwise. When the addition was complete, the cooling bath was removed and the solution was warmed slowly to room temperature and subsequently stirred for 1.5 hours. After the suspension had been cooled to 0° C., 10.1 g of chlorotributyltin (0.031 mol) were added dropwise. The suspension formed was warmed to room temperature and stirred for 1.5 hours. The ether was removed in vacuo and the crude product was dissolved again in hexane, the solution was filtered and the filtrate was dried in vacuo, 16.6 g of the compound 19 (yield: 97%) remaining as a heavy yellow oil. Two isomers were obtained in a ratio of 1.5:1. The main isomer was identified as follows: $^1$H-NMR (400 MHz, CD$_2$Cl$_2$): δ7.71 (d, J=7.2 Hz, 1 H), 7.41 (d, J=7.3 Hz, 1 H), 7.13 (m, 2 H), 6.96 (m, 1 H), 4.28 (s with Sn satellites, 1 H), 2.21 (m, 1 H), 1.54 (m, 1 H), 1.45–0.65 (m, 39 H). $^{31}$P-NMR (161.9 MHz, CD$_2$Cl$_2$): δ–11.3 ppm. The secondary isomer was identified as follows: $^1$H-NMR (400 MHz, CD$_2$Cl$_2$) δ7.6 (d, J 7.4 Hz, 1 H), 7.46 (d, J=7.2 Hz, 1 H), 7.26 (t, J=7.5 Hz, 1 H), 7.1 (m, 1 H), 6.71 (m, 1 H), 3.48 (m, 1 H), 2.21 (m, 1 H), 1.54 (m, 1 H), 1.45–0.65 (m, 39 H). $^{31}$P-NMR (161.9 MHz, CD$_2$Cl$_2$): d–11.5 ppm.

Example 19
(Diisopropylphosphino-indenyl-zirconium trichloride, compound 20)

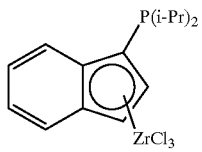

20

A solution of 15.0 g of the compound 19 (0.029 mol) in 50 ml of toluene was added dropwise to a suspension of 6.7 g (0.029 mol) of 99.9% pure ZrCl$_4$ in 300 ml of toluene at –78° C. When the addition was complete, the reaction mixture was stirred at –30° C. for 0.5 hour and then at 0° C. for 4 hours. The yellow precipitate which formed was filtered off and washed with toluene and hexane. The solids were dried in vacuo, 8.8 g of the compound 20 (yield: 71%) remaining as a free-flowing yellow powder. The powder was further purified by removal of the remaining tin compounds by means of extraction with toluene fed under reflux over a period of 3 hours under 30 mm Hg and then with pentane over a period of 2 hours in a Soxhlet extractor. Because of the insolubility of the compound formed, no $^1$H-NMR was obtained.

Example 20
(Diisopropylphosphino-dichloroboranyl-bridged indenyl-cyclopentadienyl-zirconium dichloride, compound 21)

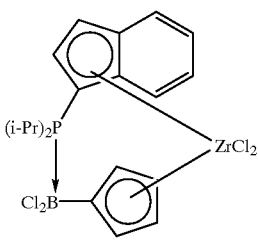

21

0.52 g (0.0012 mol) of the compound 20 and 30 ml of toluene were introduced into a Schlenk tube. 0.27 g (0.0012 mol) of the compound 2 were added to this suspension in the course of 5 minutes. The yellow suspension was stirred at room temperature for 3 hours, a slightly cloudy solution remaining. The precipitate was removed by filtration, a pale yellow toluene solution remaining. After removal of the toluene in vacuo, the product remained as a whitish solid in an amount of 0.47 g (yield: 87%). $^1$H-NMR (400 MHz, CD$_2$Cl$_2$) δ 7.84 (pseudo dd, J=8.5, 0.8 Hz, 1 H), 7.73 (d, J=8.8 Hz, 1 H), 7.5 (pseudo dt, J=7.8, 0.8 Hz, 1 H), 7.38 (m, 2 H), 6.98 (m, 1 H), 6.67 (m, 1 H), 6.64 (m, 1 H), 6.54 (m, 1 H), 6.29 (m, 1 H), 3.39 (septet, J=7.1 Hz, 1 H), 2.94 (m, 1 H), 1.68 (dd, J$_{H-P}$=18.1 Hz, J=7.2 Hz, 3 H), 1.64 (dd, J$_{H-P}$=17.4, J=7.2 Hz, 3 H), 1.45 (dd, J$_{H-P}$=15 Hz, J=7.2 Hz, 3 H), 1.33 (dd, J$_{H-P}$=14.6 Hz, J=7.3 Hz, 3 H). 31P-NMR (161.9 MHz, CD$_2$Cl$_2$): δ 23.1 (br, m); $^{11}$B-NMR (80 MHz, CD$_2$Cl$_2$): δ 14.8 (br d, J=110 Hz).

Example 21
(Tributylstannyl-dimethylphosphino-indene, compound 22)

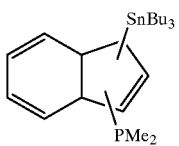

22

150 ml of ether were introduced into a round-bottomed flask which contained 5.5 g (0.047 mol) of indene; the mixture was cooled to –20° C. 20.8 ml of a 2.3 molar solution of butyl-lithium in hexane (0.048 mol) were added to this solution in the course of 5 minutes, a yellow solution being formed. After removal of the cooling bath, the solution was warmed to room temperature and subsequently stirred for 1 hour. After the reaction mixture had been cooled to –30° C., 4.6 g of chlorodimethylphosphine (0.048 mol) in 30 ml of ether were added in the course of 20 minutes, a precipitate forming. After stirring at –20° C. for 2 hours, 20.8 ml of a 2.3 molar solution of butyl-lithium in hexane (0.048 mol) were added dropwise. When the addition was complete, the cooling bath was removed and the solution was warmed slowly to room temperature and subsequently stirred for 1.5 hours. After the suspension had been cooled to 0° C., 15.6 g of chlorotributyltin (0.048 mol) were added dropwise. The suspension formed was warmed to room temperature and stirred for 1.5 hours. The ether was removed in vacuo and the crude product was dissolved again in hexane, the solution was filtered and the filtrate was dried in vacuo, 17.4 g of the compound 22 (yield: 78%) remaining as a heavy yellow oil. $^1$H-NMR (400 MHz, CD$_2$Cl$_2$) δ 7.67 (d, J=7.5 Hz, 1 H), 7.47 (d, J=7.4 Hz, 1 H), 7.18 (m, 2 H), 6.83 (m, 1 H), 4.28 (s with Sn satellites, 1 H), 1.43–0.78 (m, 33 H). $^{31}$P-NMR (161.9 MHz, CD$_2$Cl$_2$): δ–61.6 ppm.

Example 22
(Dimethylphosphino-indenyl-zirconium trichloride, compound 23)

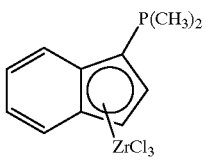

23

A solution of 17.0 g of the compound 22 (0.037 mol) in 50 ml of toluene was added to a suspension of 8.5 g (0.036 mol) of 99.9% pure ZrCl₄ in 200 ml of toluene at −78° C. When the addition was complete, the reaction mixture was stirred at −30° C. for 0.5 hour and then at 0° C. for 4 hours. The yellow precipitate formed was filtered off and washed with toluene and hexane. The solids were dried in vacuo, 8.3 g of the compound 23 (yield: 61%) remaining as a free-flowing yellow powder. The powder was further purified by removal of the remaining tin compounds by means of extraction with toluene fed under reflux over a period of 3 hours under 30 mm Hg and then with pentane over a period of 2 hours in a Soxhlet extractor, 7.2 g (yield: 53%) of the product remaining. Because of the insolubility of this compound, no $^1$H-NMR was obtained.

Example 23
(Dimethylphosphino-dichloroboranyl-bridged indenyl-cyclopentadienyl-zirconium dichloride, compound 24)

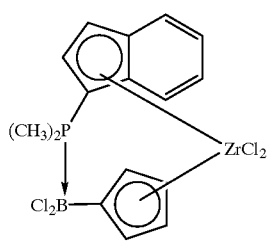

24

30 ml of toluene and 0.55 g of the compound 23 (0.0015 mol) were introduced into a Schlenk tube. 0.31 g (0.0014 mol) of the compound 2 were added to this suspension in the course of 5 minutes. The yellow suspension was stirred at room temperature for 6.5 hours, a slightly cloudy solution remaining. The precipitate was removed by filtration, a pale yellow toluene solution remaining. After removal of the toluene in vacuo, the product remained as a whitish solid. After the product had been washed with hexane and dried in vacuo, the compound 24 remained as a pale white solid (0.54 g; yield: 76%). $^1$H-NMR (400 MHz, CD$_2$Cl$_2$) δ 7.84 (pseudo dd, J=7.4 Hz 1.0 Hz, 1 H), 7.60 (m, 2 H), 7.51 (m, 1 H), 7.38 (m, 1 H), 6.93 (m, 1 H), 6.71 (m, 1 H), 6.66 (m, 1 H), 6.49 (m, 1 H), 6.30 (br s, 1 H), 2.11 (d J$_{H-P}$=11.9 Hz, 3 H), 1.94 (d, J$_{H-P}$=11.9 Hz, 3 H). $^{31}$P-NMR (161.9 MHz, CD$_2$Cl$_2$)−5.9 (br, m); $^{11}$B-NMR (80 MHz, CD$_2$Cl$_2$) δ−14.6 (br d, J$_{B-P}$= 126 Hz).

Example 24
(2-Methylindene, compound 26)

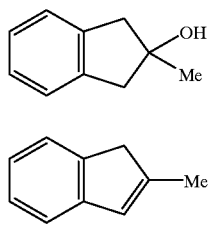

25

26

38.7 g (0.29 mol) of 2-indanone and 300 ml of ether were introduced into a round-bottomed flask. 96.7 ml of a 3.0 molar solution of CH₃MgI in ether (0.29 mol), which was diluted with 150 ml of ether, were introduced into a second flask. Thereafter, the 2-indanone solution was added to the CH₃MgI solution via a cannula in an amount such that the reflux was maintained, a precipitate being formed. When the addition was complete, the suspension was kept under reflux for a further 4 hours and cooled to 0° C., after which 100 ml of a saturated solution of NH₄Cl were slowly added. The product was extracted with ether and dried over MgSO₄. After removal of the solvent in vacuo, 30.1 g (yield: 70%) of 2-methyl-2-indanol (compound 25) were obtained as an oily solid. $^1$H-NMR (400 MHz, CDCl₃) δ 7.15 (br m, 4 H), 3.01 (s, 2 H), 2.99 (s, 2 H), 1.5 (s, 3 H); OH variable.

25.5 g (0.17 mol) of the compound 25, 3.2 g (0.017 mol) of p-toluenesulfonic acid and 500 ml of hexane were introduced into a round-bottomed flask with a Dean-Stark collecting vessel. This suspension was kept under reflux for 3 hours. After cooling, the hexane fraction was decanted from the insoluble products and the solvent was removed in vacuo to leave an oil which was then distilled in a short distillation column at 45° C. under 0.03 mbar, whereupon 15 g (yield: 68%) of the compound 26 were obtained. $^1$H-NMR (400 MHz, CDCl₃) δ 7.33 (d, J=7.6 Hz, 1 H), 7.21 (m, 2 H), 7.06 (pseudo d t, J=7.2, 1.4 Hz, 1 H), 6.45 (br s, 1 H), 3.25 (s, 2 H), 2.12 (s, 3 H).

Reference is made to:
1. Morrison, H; Giacherio, D. *J. Org. Chem.* 1982, 47, 1058.
2. Ready, T. E.; Chien, J. C. W.; Rausch, M. D. *J. Organorn. Chem.* 591, 1996, 21.
3. Wilt, Pawlikowki, Wieczorek *J. Org. Chem.* 37, 1972, 824.

Example 25
(Tributylstannyl-diisopropylphosphino-2-methylindene, compound 27)

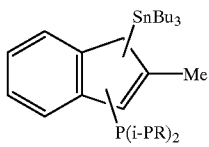

27

150 ml of ether were introduced into a round-bottomed flask which contained 5.08 g (0.039 mol) of 2-methylindene 26; the mixture was cooled to −20° C. 17.0 ml of a 2.3 molar solution of butyl-lithium in hexane (0.039 mol) were added to this solution in the course of 5 minutes, a yellow solution being formed. After removal of the cooling bath, the solution was warmed to room temperature and subsequently stirred for 1 hour. Thereafter, the reaction mixture was cooled to −20° C. and 5.8 g (0.039 mol) of chlorodiisopropylphosphine were added in the course of 5 minutes, a precipitate being formed. Thereafter, the cooling bath was removed and the reaction mixture was stirred at room temperature for 1 hour. After cooling to −20° C., 17.0 ml of a 2.3 molar solution of butyl-lithium in hexane (0.039 mol) were added dropwise. When the addition was complete, the cooling bath was removed and the solution was warmed slowly to room temperature and subsequently stirred for 1.5 hours. After the suspension had been cooled to 0° C., 12.4 g (0.038 mol) of chlorotributyltin were added dropwise. The suspension formed was heated to room temperature and stirred for 1.5 hours. The ether was removed in vacuo and the crude product was dissolved again in hexane, the solution was filtered and the filtrate was dried in vacuo, 20.4 g (yield: 98%) of the compound 27 remaining as a heavy yellow oil. Two isomers were identified by $^{31}$P-NMR. $^{31}$P-NMR (161.9 MHz, CD₂Cl₂) δ−5.9 and −6.6 in a ratio of 2:1.

Example 26
(Diisopropylphosphino-2-methylindenyl-zirconium trichloride, compound 28)

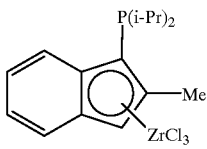

A solution of 17.7 g (0.033 mol) of the compound 27 in 100 ml of methylene chloride was added to a suspension of 7.7 g (0.033 mol) of 99.9% pure $ZrCl_4$ in 200 ml of methylene chloride at −25° C. in the course of 10 minutes. When the addition was complete, the reaction mixture was warmed slowly to 10° C. over a period of 3 hours, after which a clear, orange-colored solution was formed. After 1 hour at room temperature, the solvent was removed in vacuo and the oil formed was washed with 2×50 ml of hexane, whereupon an oily crude product (28) was obtained, this being used directly for the preparation of the compound 29. Because of the insolubility of this compound, no $^1$H-NMR was obtained.

Example 27
(Diisopropylphosphino-dichloroboranyl-bridged 2-methylindenyl-cyclopentadienyl-zirconium dichloride, compound 29)

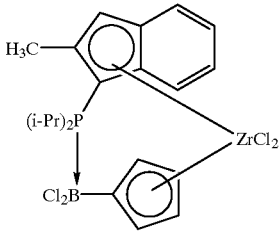

5.5 g (0.025 mol) of the compound 2 were introduced into a round-bottomed flask which contained 0.025 mol of the impure compound 28 in 200 ml of toluene at 0° C., over a period of 5 minutes. After 1 hour at 0° C., the stirring was ended and the soluble toluene fraction was decanted from the oil formed. After removal of the toluene in vacuo, 100 ml of hexane were added to the oily solid, 7.4 g (yield: 54%) of a yellow powder being formed with a purity of about 90%. The product was further purified in a Soxhlet extraction apparatus with pentane fed under reflux. The end product comprised a pale yellow powder. $^1$H-NMR (400 Mrz, $CD_2Cl_2$) δ 8.67 (br d, J=7.6 Hz, 1 H), 7.71 (m, 1 H), 7.35 (m, 2 H), 6.62 (br s, 1 H), 6.54 (br s, 1 H), 6.47 (m, 1 H), 6.33 (m, 1 H), 6.06 (br s, 1 H), 3.3 (br m, 1 H), 3.2 (br m, 1 H), 2.6 (s, 3 H), 1.78 (dd, J=7.1 Hz, $J_{H-P}$=15.3 Hz, 3 H), 1.70 (dd, J=7.2 Hz, $J_{H-P}$=15.7 Hz, 3 H). 1.57 (dd, J=7.1 Hz, $H_{H-P}$=15.3 Hz, 3 H), 1.12 (dd, J=7.1 Hz, $J_{H-P}$=14.0 Hz, 3H). 31P-NMR (161.9 MHz, $CD_2Cl_2$) 28.4 (br m); $^1$B-NMR (80 MHz, $CD_2Cl_2$) δ−14.3 (br d, $J_{P-B}$=106 Hz).

Example 28
(Bis(trimethylsilyl)-diphenylphosphino)-cyclopentadiene, compound 30)

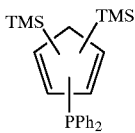

TMS = -Si(CH$_3$)$_3$ 76.6 ml of a 2.5 molar solution of butyl-lithium in hexane (0.19 mol) were added to a solution of the compound 1 (40.2 g; 0.19 mol) in 500 ml of ether at 0° C. in the course of 10 minutes. When the addition was complete, the bath was removed and the solution was stirred at room temperature for 1 hour. After cooling to 0° C., 42.2 g (0.19 mol) of chlorodiphenylphosphine were added in the course of 10 minutes, after which the bath was removed and the suspension was warmed to room temperature. After stirring at room temperature for 1 hour, the ether was removed in vacuo and the product was dissolved again in hexane. After the salts had been filtered off, the hexane was removed in vacuo, 69.1 g (yield. 91%) of the compound 30 remaining as an oil. $^1$H-NMR (400 MHz, $CDCl_3$) δ 7.45 (m, 4H), 7.35 (m, 6H), 6.8 (m, 1 H), 6.65 (m, 1 H), 6.6 (m, 1H), 0 (s 18 H). $^{31}$P-NMR (161.9 MHz, $CDCl_3$): δ−19.5 ppm.

Example 29
(Trimethylsilyl-diphenylphosphino-cyclopentadienyl-zirconium trichloride, compound 31)

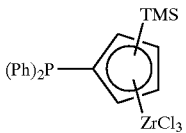

A solution of the compound 30 (69.1 g, 0.175 mol) in 200 ml of methylene chloride was added to a suspension of 41.5 g (0.178 mol) of 99.9% pure $ZrCl_4$ in 200 ml of methylene chloride via a cannula and the mixture was stirred at room temperature for 8 hours. During this period, the solution became cloudy. The solids were filtered off, washed with 2×20 ml of toluene and then 2×20 ml of hexane and dried in vacuo. The product comprised 35 g (yield: 39%) of a pale yellow powder. Because of the insolubility of the product, no $^1$H-NMR was obtained.

Example 30
(Diphenylphosphino-dichloroboranyl-bridged trimethylsilylcyclopentadienyl-cyclopentadienyl-zirconium dichloride, compound 32)

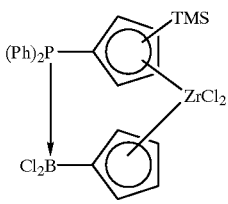

A solution of the compound 2 (2.6 g, 0.012 mol) was added to a suspension of the compound 31 (5.6 g, 0.011 mol) in 100 ml of toluene at 0° C. After the mixture had been stirred at 0° C. for 5 hours, the yellow-brown solid was removed by filtration, a whitish solution remaining. After removal of the toluene in vacuo and washing of the solid which remained with pentane, the compound 32 remained as a highly air-sensitive whitish powder (5.5 g; yield: 81%). $^1$H-NMR (400 MHz, CD$_2$Cl$_2$) δ: 7.8–7.5 (m, 10 H), 7.06 (m, 1 H), 6.92 (m, 1 H), 6.83 (m, 1 H), 6.75 (m, 2 H), 6.68 (m, 1 H), 6.63 (m, 1 H), 0.26 (s, 9 H). $^{31}$P-NMR (161.9 MHz, CD$_2$Cl$_2$) δ: 0 (br, m); $^{11}$B-NMR (80 MHz, CD$_2$Cl$_2$) δ–16.3 (br d, $J_{B-P}$=82 Hz).

Example 31

(Diisopropylphosphino-cyclopentadienyl-lithium, compound 33)

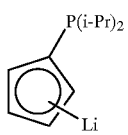

33

50 ml of ether were introduced into a round-bottomed flask which contained 1.68 g (0.023 mol) of cyclopentadienyl-lithium. After the reaction flask had been cooled to −20° C., 3.6 g (0.023 mol) of chlorodiisopropylphosphine were added dropwise. When the addition was complete, the cooling bath was warmed to 0° C. and the reaction mixture was stirred for 1 hour. Thereafter, ether was removed in vacuo, the product was dissolved in toluene and the solution was filtered. After the frit had been rinsed through with 2×10 ml of toluene, the reaction mixture was cooled to −20° C. and 9.3 ml of a 2.5 molar solution of butyllithium in hexane (0.023 mol) were added, an orange-colored solution being formed. A small fraction was taken for NMR analysis and, after removal of the toluene in vacuo and washing of the oil formed with hexane, a pale yellow solid (33) was obtained. $^1$H-NMR (400 MHz, THF) δ: 5.89 (m, 2 H), 5.83 (br s, 2 H), 1.86 (m, 2 H), 1.0–0.8 (m, 12 H). The main amount was used directly for the preparation of the compound 34.

Example 32

(Diisopropylphosphino-dimethylboranyl-bridged bis-cyclopentadienyl-titanium dichloride, compound 34)

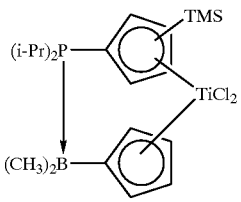

34

A solution of 6.1 g (0.023 mol) of the compound 4 in 50 ml of toluene was added to a toluene solution of the compound 33 (0.023 mol) from the abovementioned reaction at −78° C. After the mixture had been stirred at −78° C. for 30 minutes, the cooling bath was removed and the solution was subsequently stirred at room temperature for 2 hours. Thereafter, the solids were removed by filtration and the toluene was removed in vacuo. Hexane was then added to the red oily product, a red powder being formed, which was filtered off, washed with 2×20 ml of hexane and dried in vacuo, whereupon the compound 34 was formed as a red powder (5.95 g, yield, based on CpLi: 61%). $^1$H-NMR (400 MHz, CD$_2$Cl$_2$) δ: 6.96 (m, 2 H), 6.94 (pseudo t, J=2.4 Hz, 2 H), 6.59 (m, 2 H), 6.42 (m, 2 H), 2.58 (m, 2 H), 1.44 (dd, J=7.3 Hz, $J_{H-P}$=14.7 Hz, 6 H), 1.27 (dd, J=7.2 Hz, $J_{H-P}$=13.1 Hz, 6 H), 0.31 (d, $J_{H-P}$=16.4 Hz, 6 H). $^{31}$P-NMR (161.9 MHz, CD$_2$Cl$_2$) δ 28.7 (br m); $^{11}$B-NMR (80 MHz, CD$_2$Cl$_2$) δ–29.7 (br m).

Example 33

(Dimethylphosphino-tributylstannyl-2-methylindene, compound 35)

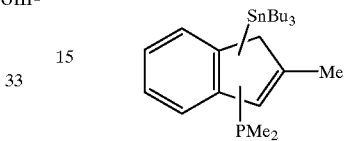

35

100 ml of ether were introduced into a round-bottomed flask which contained 6.76 g (0.052 mol) of 2-methylindene (compound 26); the mixture was cooled to −20° C. 21 ml of a 2.5 molar solution of butyl-lithium in hexane (0.052 mol) were added to this solution in the course of 5 minutes, a yellow solution being formed. After removal of the cooling bath, the solution was warmed to room temperature and subsequently stirred for 1 hour. After the reaction mixture had been cooled to −20° C., 5.0 g (0.052 mol) of chlorodimethylphosphine were added in the course of 5 minutes, a precipitate being formed. The cooling bath was then removed and the reaction mixture was stirred at room temperature for 1 hour. After cooling to −20° C., 21.0 ml of a 2.5 molar solution of butyl-lithium in hexane (0.052 mol) were added dropwise. When the addition was complete, the cooling bath was removed, after which the solution was warmed slowly to room temperature and stirred for 1.5 hours. After the suspension had been cooled to 0° C., 16.9 g (0.052 mol) of chlorotributyltin were added dropwise. The suspension formed was warmed to room temperature and stirred for 1.5 hours. After removal of the ether in vacuo, the crude product was dissolved again in hexane, the solution was filtered and the filtrate was dried in vacuo, 24.3 g (yield: 98%) of the compound 35 remaining as a heavy yellow oil. $^{31}$P-NMR (161.9 MHz, CD$_2$Cl$_2$) δ–68.5 (s).

Example 34

(Dimethylphosphino-2-methylindenyl-zirconium trichloride, compound 36)

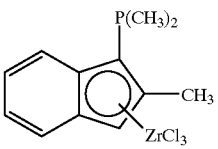

36

A solution of 17.4 g (0.036 mol) of the compound 35 in 100 ml of toluene was added to a suspension of 8.5 g (0.036 mol) of 99.9% pure ZrCl$_4$ in 100 ml of toluene at 0° C. in the course of 10 minutes. When the addition was complete, the reaction mixture was warmed slowly to 10° C. over a period of 1 hour and then stirred at room temperature for 6 hours. The yellow precipitate was subsequently filtered off, washed with 2×20 ml of toluene and 2×20 ml of hexane and dried in vacuo. The powder was further purified by removal of the remaining tin compounds by means of extraction with toluene fed under reflux over a period of 3 hours under 30 mm Hg and then with pentane over a period of 2 hours in a Soxhlet extractor, 5.8 g (yield: 41%) of the compound 36 remaining as a luminous yellow powder. Because of the insolubility of this compound, no $^1$H-NMR was obtained.

Example 35
(Dimethylphosphino-dichloroboranyl-bridged 2-methylindenyl-cyclopentadienyl-zirconium dichloride, compound 37)

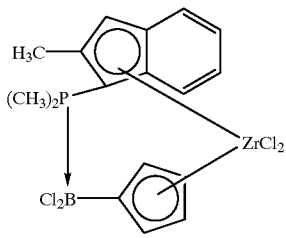

37

2.7 g (0.012 mol) of the compound 2 were introduced into a round-bottomed flask, which contained 4.8 g (0.012 mol) of the compound 36 in 125 ml of toluene at room temperature, in the course of 5 minutes. After the mixture had been stirred for 7 hours, the dark yellow solid was filtered off, washed with 2×20 ml of hexane and dried in vacuo, 5.5 g (yield: 89%) of the compound 37 being obtained as a pale yellow solid. $^1$H-NMR (400 MHz, CD$_2$Cl$_2$) δ 8.39 (d, J=8.5 Hz, 1 H), 7.71 (m, 1 H), 7.4 (m, 2 H), 6.64 (m, 2 H), 6.46 (pseudo q, J=5.3, 2.9 Hz, 1 H), 6.37 (m, 1 H), 6.08 (m, 1 H), 2.51 (s, 3 H), 2.1 (d, $J_{H-P}$=12 Hz, 3 H), 2.0 (d, $J_{H-P}$=12 Hz, 3 H); $^{31}$P-NMR (161.9 MHz, CD$_2$Cl$_2$) 5.3 (br m); $^{11}$B-NMR (80 MHz, CD$_2$Cl$_2$) δ–16.5 (br d, $J_{B-P}$=116 Hz).

Example 36
(Dicyclohexylboranylcyclopentadienyl-lithium, compound 39)

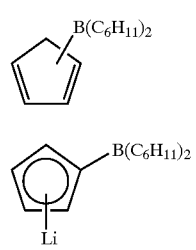

38

39

Reference is made to: Herberich, G. E.; Fischer, A. *Organometallics* 1996, 15, 58.

40 ml of a 1 molar solution of chlorodicyclohexylborane in hexane (0.04 mol) were added to 20 ml of cyclopentadienyl-sodium (2 M in THF; 0.04 mol) in 100 ml of hexane at –78° C. After removal of the cooling bath, the reaction mixture was warmed to room temperature and stirred for 1 hour. After filtration and removal of the solvent in vacuo, 9.1 g (yield: 94%) of the compound 38 remained as a yellow oil, which was used directly in the synthesis of the compound 39.

5.3 g (0.038 mol) of 2,2,6,6-tetramethylpiperidine were introduced into a round-bottomed flask which contained 40 ml of THF. After cooling to –20° C. and addition of 15 ml of a 2.5 molar solution of butyl-lithium in hexane (0.038 mol), the mixture was stirred at –20° C. for 1 hour and then cooled to –78° C. 9.1 g (0.038 mol) of the compound 38 in 20 ml of hexane were added to this solution in the course of 10 minutes. The cooling bath was removed and the solution was stirred at room temperature for 1 hour. After removal of the solvent in vacuo and addition of hexane, the mixture was subsequently stirred for 2 hours, a white suspension being formed, which was filtered, and the product was dried in vacuo. 4.6 g (yield: 50%) of the compound 39 were formed as a white powder. $^{11}$B-NMR (80 MHz, THF) δ43.9.

Example 37
(Diphenylphosphino-dicyclohexylboranyl-bridged trimethylsilyl-cyclopentadienyl-cyclopentadienyl-zirconium dichloride, compound 40)

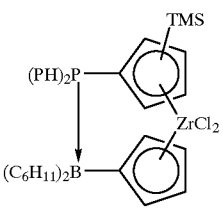

40

After cooling a Schlenk flask which contained 1.4 g (0.0056 mol) of the compound 39 and 2.9 g (0.0056 mol) of the compound 31 to –20° C., 100 ml of toluene were added. After removal of the bath, the suspension was stirred at room temperature for 6 hours and then filtered. The solvent was removed in vacuo, an oily solid remaining, which was washed with hexane and filtered. After the solid had been dried in vacuo, 1.9 g (yield: 48%) of the compound 40 remained as a pink-colored solid. $^1$H-NMR (400 MHz, CD$_2$Cl$_2$) δ 7.6–7.2 (br m, 10 H), 7.04 (br s, 1 H), 6.95 (m, 1 H), 6.82 (m, 1 H), 6.76 (br s, 1 H), 6.66 (m, 1 H), 6.63 (m, 1 H), 6.52 (m, 1 H), 1.6–1.1 (br m, 22 H), 0.26 (s, 9 H); $^{31}$P-NMR (161.9 MHz, CD$_2$Cl$_2$) δ 16.3; $^{11}$B-NMR (80 MHz, CD$_2$Cl$_2$) δ–13.8.

Example 38
(4,7-Dimethylindene, compound 41)

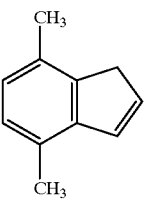

41

Reference is made to: Erker, G. et al. *Tetrahedron* 1995, 51, 4347.

A 30% strength solution of 153 g (2.8 mol) of sodium methoxide in methanol was diluted with 60 ml of methanol and cooled to 0° C. 34 g (0.52 mol) of cyclopentadiene were added to this solution. After 15 minutes, 39 g (0.34 mol) of 2,5-hexanedione were added dropwise, after which the cooling bath was removed and the reaction mixture was stirred at room temperature for 2 hours. 200 ml of water and 200 ml of ether were then added. The ether layer was removed, washed with water and sodium chloride solution and then dried over Na$_2$SO$_4$. After removal of the solvent in vacuo and distillation at 65° C. under 0.1 mbar, the compound 41 remained as an orange-colored oil (40 g; yield: 81%). ¹H-NMR (400 MHz, CDCl₃) δ 7.35–7.27 (m, 2 H), 7.23 (d, J=7.6 Hz, 1 H), 6.82 (m, 1 H), 3.51 (s, 2 H), 2.75 (s, 3H), 2.63 (s, 3 H).

Example 39
(Diisopropylphosphino-tributylstannyl-4,7-dimethylindene, compound 42)

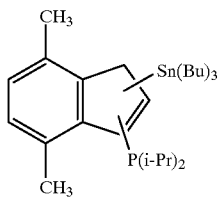

100 ml of ether were introduced into a round-bottomed flask which contained 5.0 g (0.035 mol) of 4,7-dimethylindene (compound 41); the mixture was cooled to −20° C. 14 ml of a 2.5 molar solution of butyl-lithium in hexane (0.035 mol) were added to this solution in the course of 5 minutes, a yellow solution being formed. After removal of the cooling bath, the solution was warmed to room temperature and subsequently stirred for 1 hour. After the reaction mixture had been cooled to −20° C., 5.3 g (0.035 mol) of chlorodiisopropylphosphine were added in the course of 5 minutes, a precipitate being formed. Thereafter, the cooling bath was removed and the reaction mixture was stirred at room temperature for 1 hour. After cooling to −20° C., 14.0 ml of a 2.5 molar solution of butyllithium in hexane (0.035 mol) were added dropwise. When the addition was complete, the cooling bath was removed and the solution was warmed slowly to room temperature and stirred for 1.5 hours. After the suspension had been cooled to 0° C., 11.4 g of chlorotributyltin (0.035 mol) were added dropwise. The suspension formed was warmed to room temperature and stirred for 1.5 hours. The ether was removed in vacuo and the crude product was dissolved again in hexane, the solution was filtered and the filtrate was concentrated in vacuo, 16 g (yield: 83%) of the compound 42 remaining as a heavy yellow oil. ³¹P-NMR (161.9 MHz, CD₂C₂) δ−9 ppm.

Example 40
(Diisopropylphosphino-4,7-dimethylindenyl-zirconium trichloride, compound 43)

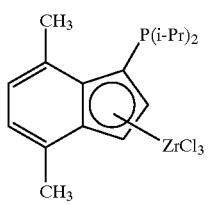

A solution of 16.0 g (0.029 mol) of the compound 42 in CH₂Cl₂ (100 ml) was added to a suspension of 6.4 g (0.029 mol) of 99.9% pure ZrCl₄ in 100 ml of CH₂Cl₂ at −20° C. in the course of 10 minutes. When the addition was complete, the reaction mixture was warmed slowly to room temperature over a period of 2 hours and then stirred at room temperature for a further two hours. Thereafter, the solids were removed by filtration and the solvent was removed in vacuo, the crude compound 43 remaining as an oil which was used directly for the preparation of the compound 44.

Example 41
(Diisopropylphosphino-dichloroboranyl-bridged 4,7-dimethylindenyl-cyclopentadienyl-zirconium dichloride, compound 44)

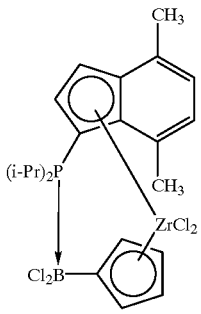

5.0 g (0.023 mol) of the compound 2 were introduced into a round-bottomed flask, which contained 10.6 g (0.023 mol) of the compound 43 in 125 ml of toluene at 0° C., in the course of 5 minutes. After the mixture had been stirred at 0° C. for 1.5 hours, the cooling bath was removed and the suspension was stirred at room temperature for a further 3 hours. Thereafter, the toluene-soluble fraction was decanted from the heavy oil which had formed during the reaction, and was concentrated to dryness in vacuo, a heavy oil remaining. After addition of 100 ml of hexane to this oil, the mixture was subsequently stirred and a dark yellow powder was filtered off and was dried in vacuo. After this process, 6.3 g (yield: 48%) of the compound 44 remained as a dark yellow powder. The product can be further purified by precipitation of a CH₂Cl₂ solution of the compound 44 in a hydrocarbon solvent. ¹H-NMR (400 MHz, CD₂Cl₂) δ 8.03 (pseudo t, J=8.5 Hz, 1 H), 7.22 (d, J=7 Hz, 1 H), 7.08 (d, J=7.1 Hz, 1 H), 7.02 (m, 1 H), 6.77 (m, 1 H), 6.70 (m, 1 H), 6.58 (m, 1 H), 6.44 (br s, 1 H), 3.51 (m, 1 H), 2.82 (m, 1 H), 2.64 (s, 3 H), 2.50 (s, 3 H), 1.77 (dd, J=7.2 Hz, $J_{H-P}$=16.3 Hz, 3 H), 1.69 (dd, J=7.1 Hz, $J_{H-P}$=15.2 Hz, 3 H), 1.58 (dd, J=7.1 Hz, $J_{H-P}$=15.5 Hz, 3 H), 1.28 (dd, J=7.2 Hz, $J_{H-P}$=14.5 Hz, 3 H); ³¹P-NMR (161.9 MHz, CD₂Cl₂) δ 28.4 (br d, J=138 Hz); ¹¹B-NMR (80 MHz, CD₂Cl₂) δ−15.3 (d, J=107 Hz).

Example 42
(Pyrrole-lithium, compound 45)

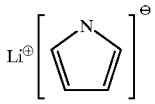

59 ml of a solution of butyl-lithium (2.5 molar in hexane, 0.148 mol) were added slowly to a solution of 9.9 g of pyrrole (0.148 mol) in 200 ml of hexane at −20° C., a white solid being formed. The mixture was subsequently stirred at room temperature for 2 hours and the solid was isolated by filtration, washed twice with 20 ml of hexane each time and dried in vacuo. This process gave 6 g of the compound 45 (56% of the theoretical yield).

¹H-NMR (400 MHz, THF): δ 6.71 (s, 2H), 5.95 (s, 2H).

Example 43
(Dimethylboranyl-bridged cyclopentadienyl-pyrrole-titanium dichloride, compound 46)

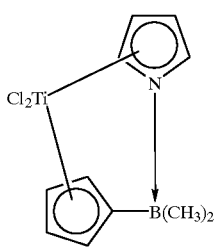

A solution of 1.34 g (0.005 mol) of the compound 4 in 20 ml of toluene was added to 0.38 g (0.005 mol) of the compound 45 at −78° C. in the course of 5 minutes. The cooling bath was then removed and stirring was continued at room temperature for 2 hours. Thereafter, the red solid which had formed was filtered off; the yellow filtrate was discarded. The red solid was washed with toluene and dried in vacuo. 1.14 g with a small content of LiCl were obtained.

$^{1}$H-NMR (400 MHz, THF): δ=6.89 (pseudo-t, J=2.3 Hz, 2 H), 6.64 (m, 2 H), 6.59 (pseudo-t, J=2.35 Hz, 2 H), 5.73 (pseudo-t, J=1.7 Hz, 2 H), 0.06 (s, 6 H). $^{11}$B-NMR (80 MHz, THF) δ=−26 ppm.

Example 44

(1-Phenyl-2,3,4,5-tetramethyl-phosphol, compound 47)

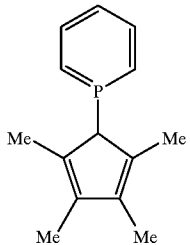

In accordance with Organometallics 7 (1988), 921, a solution of 11.7 g (0.216 mol) of 2-butine in 150 ml of CH$_2$Cl$_2$ was slowly added to 15.3 g (0.115 mol) of AlCl$_3$ in CH$_2$Cl$_2$ (0° C.; 30 minutes). The mixture was subsequently stirred at 0° C. for 45 minutes, the cooling bath was then removed and the mixture was subsequently stirred for a further hour. Thereafter, the solution was cooled to −50° C. and a solution of 21.4 g (0.12 mol) of phenyl-dichlorophosphine in CH$_2$Cl$_2$ was added in the course of 20 minutes. The cooling bath was then removed and the dark red solution was subsequently stirred for one hour and then added to a solution of 27 g (0.13 mol) of tributylphosphine in 100 ml of CH$_2$Cl$_2$ at −30° C. The red color disappeared immediately; a yellow solution remained. When the addition had ended, the solvent was removed in vacuo; a thick yellow oil remained. The oil was taken up in hexane and washed with saturated aqueous NaHCO$_3$ solution and H$_2$O under an Ar atmosphere. After drying over MgSO$_4$, the hexane was removed in vacuo. 18.2 g remained as a clear oil (yield 78%). $^{1}$H-NMR (400 MHz, CDCl$_3$) δ: 7.3 (m, 5H), 2.0 (m, 12H), $^{31}$P-NMR (161.9 MHz, CDCl$_3$) δ: 16.8 ppm.

Example 45

(Lithium-2,3,4,5-tetramethyl-phosphol, compound 48)

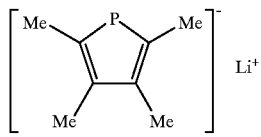

In accordance with Organometallics 7 (1988), 921, 0.52 g (0.074 mol) of lithium was added to a solution of 7 g (0.032 mol) of the compound 47 in 150 ml of tetrahydrofuran (THF) and the mixture was stirred overnight. The resulting red solution was filtered through a frit to remove residual solids and the filtrate was cooled to 0° C. Thereafter, a solution of 1.45 g (0.01 mol) of AlCl$_3$ in 20 ml of THF was added dropwise and the solution was brought to room temperature. An aliquot amount was removed for analysis and the remaining solution was used directly for the preparation of the compound 49. $^{31}$P-NMR (161.9 MHz, THF) δ: 63.7 ppm.

Example 46

(Dimethylboranyl-cyclopentadienyl-tetramethylphospholtitanium dichloride, compound 49)

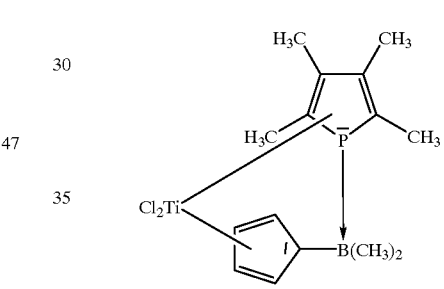

The THF solution from Example 45 with 1.46 g (0.01 mol) of the compound 48 was introduced into a round-bottomed flask; the THF was removed in vacuo. After addition of toluene and cooling to −78° C., a solution of 2.6 g (0.01 mol) of the compound 44 in 20 ml of toluene was slowly added while stirring, a red suspension being formed. When the addition had ended, the suspension was brought to room temperature and subsequently stirred for 1 hour. After solid which remained undissolved had been filtered off, the toluene was removed in vacuo; hexane was added to the oily solid which remained. The solid which remained undissolved was also filtered off from the hexane solution and the solution was stored overnight at −20° C. After the hexane had been decanted off, 0.5 g of a green solid which was identified as compound 49 (yield 14%) was obtained. $^{1}$H-NMR (200 MHz, CD$_2$Cl$_2$) δ: 6.64 (m, 2H), 6.57 (m, 2H), 2.11 (d, J$_{H-P}$=10 Hz, 6H), 2.09 (s, 6H), 0.87 (d, J$_{H-P}$=5.3 Hz, 6H). $^{31}$P-NMR (161.9 MHz, THE) δ: 95.6 ppm, $^{11}$B-NMR (80 MHz, CD$_2$Cl$_2$) δ: 39 (br, m) ppm.

Example 47

(Ethylene polymerization)

50 ml of dry oxygen-free toluene was sucked into a dry, O$_2$-free, magnetically stirred V4A steel autoclave which had been thoroughly heated in vacuo. The D/A-metallocene catalyst (compound 10) was preformed in toluene at room temperature with MAO (methylaluminoxane, 10% strength in toluene, molecular weight 900 g/mol) in an atom(mol)

ratio of Al/Zr=66,666: 1 in 15 minutes. An aliquot which contained $1.5 \times 10^{-7}$ mol of Zr and $1.0 \times 10^{-2}$ mol of Al in 6.8 ml was injected into the autoclave with strict exclusion of air and the autoclave was subsequently flushed with a further 50 ml of toluene. Polymerization was then carried out under a constant ethylene pressure of 10 bar at room temperature for 1 hour, the internal temperature rising to 42° C. After the autoclave had been let down, the reaction mixture was introduced into 500 ml of ethanol and 50 ml of concentrated aqueous hydrochloric acid and stirred overnight, and the polymer was filtered off, washed thoroughly with ethanol and dried to constant weight at 100° C. in a circulating air drying cabinet. The PE yield was 2.9 g, which corresponds to a catalyst activity of 19.3 tonnes of polymer per mole of Zr and hour. The limiting viscosity, measured in o-dichlorobenzene at 140° C., was 4.36 dl/g. The DSC measurement gave a melting point of 139° C. and a heat of fusion of 164 J/g.

Examples 48 to 51
(Ethylene polymerization)

In other ethylene polymerization experiments, the procedure was as in Example 47, but the D/A-metallocene 7 was used as the catalyst and different amounts of MAO were employed. The amount of Ti was $1 \times 10^{-6}$ mol and the autoclave was heated to about 100° C. The Al/Zr ratio was varied between 1250, 2500, 5000 and 10,000. In all 4 experiments, the catalyst activity was about 3 to 4 t of PE per mole of Ti and hour.

Example 52
(Ethylene polymerization)

The procedure was in accordance with Example 47, but 100 ml of toluene was initially introduced directly into the autoclave. The autoclave was heated to 80° C., the catalyst was injected and the ethylene pressure was adjusted to 10 bar. $1 \times 10^{-6}$ mol of the compound 18 in 2.4 ml of toluene, which had been preformed with $5 \times 10^{-3}$ mol of MAO in 3.3 mol of toluene, was used as the catalyst. The internal temperature rose from 80° C. to 94° C. After 30 minutes, the polymerization was interrupted. The PE yield was 3.5 g, which corresponds to a catalyst activity of about 7 tonnes of polymer per mole of catalyst and hour. The limiting viscosity $\eta$ was measured in ortho-dichlorobenzene at 140° C.; it was 2.95 dl/g. The DSC measurement gave a melting point of 139° C. and a heat of fusion of 165 J/g.

Examples 53 to 56
(Ethylene polymerization)

The procedure was as in Example 51. The amount of Ti (compound 7) was $1 \times 10^{-6}$ mol and the Al/Zr ratio was 10,000. The autoclave was heated to different temperatures and the polymer properties of limiting viscosity and melting point $T_m$ were measured.

| T: | RT to 60°    | = 7.2 dl/g | $T_m$ = 143° C. |
| -- | ------------ | ---------- | --------------- |
| T: | RT to 80°    | = 4.6 dl/g | $T_m$ = 142° C. |
| T: | RT to 100° C.| = 3.2 dl/g | $T_m$ = 144° C. |
| T: | RT to 120°   | = 2.2 dl/g | $T_m$ = 140° C. |

(RT - Room temperature)

Example 57
(Ethylene polymerization)

The procedure was in accordance with Example 52, but the internal temperature was adjusted to 100° C. $5 \times 10^{-7}$ mol of the compound 24 in 0.4 mol of chlorobenzene, which had been preformed with $5 \times 10^{-3}$ mol of MAO in 3.3 mol of toluene, were employed as the catalyst. The internal temperature rose from 100° C. to 120° C. After polymerization for 30 minutes, 6.2 g of PE had formed, which corresponds to a catalyst activity of about 25 tonnes of polymer per mole of catalyst and hour. The limiting viscosity $\eta$, measured in ortho-dichlorobenzene at 140° C., was 1.85 dl/g.

Example 58
(Ethylene polymerization)

The procedure was in accordance with Example 57, but the compound 21 was employed as catalyst. In this case, the internal temperature rose from 100° to 128° C. The PE yield was 7.9 g after 30 minutes, corresponding to a catalyst activity of about 31.6 tonnes per mole of catalyst and hour. The limiting viscosity $\eta$ in ortho-dichlorobenzene at 140° C. was 1.01 dl/g.

Example 59
(Ethylene polymerization)

The procedure was in accordance with Example 52, but the polymerization was started at 20° C. Metallocene 32 was used here as the catalyst. For this, $2.5 \times 10^{-7}$ mol of catalyst were preformed with $2.5 \times 10^{-3}$ mol of MAO in toluene. The internal temperature rose from 20° C. to 34° C. After polymerization for 30 minutes, 1.3 g of PE had formed, which corresponds to a catalyst activity of 10.4 tonnes of polymer per mole of catalyst and hour. The limiting viscosity $\eta$ (ortho-dichlorobenzene, 140° C.) was 5.3 dl/g.

The DSC measurement gave a melting point of 153° C. in the 1st heating up at a rate of 20 K/minute. After quenching of the sample at 320 K/minute, the melting maximum was determined at 146° C. in the 2nd heating up.

Example 60
(Ethylene polymerization)

The experiment was carried out in accordance with Example 47, but the D/A-metallocene employed as the catalyst was the compound meso-15. The amount of Zr was $5 \times 10^{-7}$ mol and the amount of Al was $1 \times 10^{-2}$ mol. After addition of the catalyst and ethylene, the autoclave was heated rapidly to about 1200° C. After a polymerization time of 30 minutes, 4.3 g of polyethylene was isolated, which corresponds to an activity of about 17 t of PE per mole of Zr and hour. The limiting viscosity 71, measured at 140° C. in o-dichlorobenzene, was 1.9 dl/g.

Example 61
(Diphenylphosphino-dichloroboranyl-bridged bis(indenyl)-zirconium dichloride, compound 50)

0.011 mol of trimethylsilyl-dichloroboranyl-indene were added to a suspension of 0.012 mol of diphenylphosphino-indenyl-zirconium trichloride in 150 ml of toluene at room temperature. The reaction mixture was then stirred at 75° C. for 1 hour. After cooling and filtration, 150 ml of hexane were added to the clear orange-colored solution, after which a heavy red oil and a pale yellow precipitate were formed; the precipitate was filtered off, washed with hexane and dried in vacuo. The pale yellow solid was identified as the pure meso compound by $^1$H-NMR spectroscopy. The filtrate with the red oil was concentrated to 30 ml and added dropwise to 200 ml of hexane, after which a second pale yellow precipitate formed, which was filtered off and dried in vacuo. This product was identified as the pure rac isomer with the aid of X-ray structure analysis. Crystals suitable for the purpose were cultured by slow diffusion of hexane into a saturated $CH_2Cl_2$ solution at the ambient temperature. The donor-acceptor bond P→B has a length of 2.02 Å. The yield was 40% and the meso/rac ratio was 1:1. If the reaction mixture was stirred for 5 hours (instead of 1 hour), at 75° C., an increased amount of the desired rac isomer was obtained; the meso/rac ratio was 1:4. At the same time, the overall yield rose slightly from 40% to 45%.

Elemental analysis: 56.05% C (theoretical 55.90%), 4.35% H (4.38%)

Spectrum meso isomer: $^1$H-NMR (400 MHz, $CD_2Cl_2$, room temperature RT): 8.01 ppm (1H, d, 8.8 Hz); 7.8–7.0 ppm (several overlapping multiplets, 28H); 6.94 ppm (1H, t, 3.3 Hz); 6.77 ppm (1H, d, 3.44 Hz); 6.31 ppm (1H, d, 8.7 Hz), $^{31}$P-NMR (161.9 MHz, $CD_2Cl_2$): 5.6 ppm. $^{11}$B-NMR (80.2 MHz, $CD_2Cl_2$): −17.0 ppm (72 Hz).

Spectrum rac isomer: $^1$H-NMR (400 MHz, $CD_2Cl_2$, RT): 8.39 ppm (1H, d, 8.5 Hz); 7.68–7.05 ppm (27H, various overlapping multiplets); 6.65 ppm (1H, d, 2.9 Hz), 6.59 ppm (1H, t, 3.5 Hz); 6.51 ppm (1H, t, 2.8 Hz); 6.40 ppm (1H, d, 3.5 Hz) $^{31}$ P-NMR (161.9 MHz, $CD_2Cl_2$): 8.1 ppm $^{11}$B-NMR (80.2 MHz, $CD_2Cl_2$)=−14.0 ppm ($J_{P-B}$ 74 Hz).

Examples 62–64

(Dialkylphosphino-dichloroboranyl-bridged bis(indenyl)-zirconium dichloride; alkyl=i-propyl=compound 51; ethyl=compound 52; methyl=compound 53)

0.016 mol of trimethylsilyl-dichloroboranyl-indene in 50 ml of toluene was added to a suspension of 0.0157 mol of dialkylphosphinoindenyl-zirconium trichloride in 250 ml of toluene at room temperature. The reaction mixture was then heated for a few hours while stirring. After cooling and filtration, 300 ml of hexane were added to the clear orange-colored solution, after which a heavy red oil and a clear yellow solution were formed. Separation of the meso and rac isomers was achieved by fractional crystallization from toluene/hexane solutions.

Characterization of the compounds (NMR spectra in $CD_2Cl_2$ at RT; $^1$H-NMR: 400 MHz, $^{31}$P-NMR: 61.9 MHz, $^{11}$B-NMR: 80.2 MHz):

rac compound 51 (i-Pr):

$^1$H-NMR: 8.41 ppm (1 H, d, 9.0 Hz); 8.31 ppm (1 H, d, 8.4 Hz); 7.84 ppm (1 H, d, 8.5 Hz); 7.64–7.24 ppm (6 H, various overlapping multiplets); 6.70 ppm (2 H, m); 6.60 ppm (1 H, m); 3.78 ppm (1 H, m, P(C$\underline{H}$($CH_3$)$_2$)$_2$; 3.21 ppm (1 H, m P(C$\underline{H}$($CH_3$)$_2$)$_2$); 1.81 ppm (6 H, m, P(CH(C$\underline{H}_3$)$_2$)$_2$; 1.72 ppm (3 H, dd, P(CH(C$\underline{H}_3$)$_2$)$_2$, 14.9 Hz, 7.3 Hz); 1.32 ppm (3 H, dd, P(CH(C$\underline{H}_3$)$_2$)$_2$, 14.1 Hz, 7.4 Hz). $^{31}$P-NMR: 22.7 ppm. $^{11}$B-NMR: −14.1 ppm (100 Hz).

Elemental analysis: 49.4% C (theoretical 48.9%), 4.6% H (4.4%).

meso compound 52 (Et):

$^1$H-NMR: 7.83 ppm (1 H, d, 9.0 Hz); 7.76 ppm (1 H, m); 7.63 ppm (1 H, d, 7.2 Hz); 7.47 ppm (1 H, d, 8.5 Hz); 7.33 ppm (2 H, m); 7.20–7.03 ppm (4 H, various overlapping multiplets); 6.76 ppm (2 H, m); 2.68 ppm (2 H, m, P(C$\underline{H}_2$CH$_3$)$_2$; 2.44 ppm (2 H, m P(C$\underline{H}_2$CH$_3$)$_2$); 1.62 ppm (3 H, m P(CH$_2$C$\underline{H}_3$)$_2$; 1.27 ppm (3 H, m, P(CH$_2$C$\underline{H}_3$)$_2$). $^{31}$P-NMR: 7.1 ppm. $^{11}$B-NMR: −15.8 ppm (100 Hz).

rac compound 52 (Et):

$^1$H-NMR: 8.28 ppm (1H, d, 8.6 Hz); 8.10 ppm (1 H, d, 8.6 Hz); 7.62 ppm (1 H, d, 8.4 Hz); 7.46 ppm (1H, d, 8.5 Hz); 7.41–7.10 ppm (4 H, various overlapping multiplets); 6.81 ppm (1 H, m); 6.47 ppm (2 H, m): 6.38 ppm (1 H, d, 3.4 Hz), 2.68 ppm (2 H, m P(C$\underline{H}_2$CH$_3$)$_2$); 2.35 ppm (2 H, m, P(C$\underline{H}_2$CH$_3$)$_2$); 1.30 ppm (6 H, m, P(CH$_2$C$\underline{H}_3$)$_2$). $^{31}$P-NMR: 12.3 ppm. $^{11}$B-NMR: −15.7 ppm.

Elemental analysis: 47.6% C (theoretical 47.1%), 4.3% H (4.0%).

meso compound 53 (Me):

$^{11}$H-NMR: 7.84 ppm (1 H, d); 7.75 ppm (1 H, d, 8.2 Hz); 7.68 ppm (1 H, d, 7.7 Hz); 7.51 ppm (1H, d, 8.5 Hz); 7.40–7.10 ppm (4 H, various overlapping multiplets); 6.77 ppm (2 H, br); 2.13 ppm (3 H, P(C$\underline{H}_3$)$_2$, d, 11.8 Hz); 1.92 ppm (3 H, P(C$\underline{H}_3$)$_2$, d, 11.8 Hz). $^{31}$P-NMR: −8.4 ppm. $^{11}$B-NMR: −16.1 ppm (103 Hz).

rac compound 53 (Me):

$^1$H-NMR: 8.21 ppm (1 H, d, 8.7 Hz); 8.15 ppm (1 H, d, 8.6 Hz); 7.63 ppm (1 H, d, 8.5 Hz); 7.44–7.07 ppm (6 H, various overlapping multiplets); 6.40 ppm (3 H, br); 2.03 ppm (3 H, d, P(C$\underline{H}_3$)$_2$, 11.9 Hz); 1.98 ppm (3 H, d, P(C$\underline{H}_3$)$_2$, 11.6 Hz). $^{31}$P-NMR: −1.5 ppm. $^{11}$B-NMR: −16.0 ppm (119 Hz).

Example 65

(1,3-Bis(trimethylsilyl)-2-methylindene, compound 54)

500 ml of hexane and 70 ml of butyllithium (as a 2.5 molar solution in hexane) were introduced into a 1000 ml flask. 0.175 mol of 2-methylindene was added dropwise at the ambient temperature; the mixture was stirred for a further 10 hours. 0.18 mol of trimethylsilyl chloride was then added dropwise at room temperature; the mixture was stirred for a further 10 hours. LiCl was filtered off and 70 ml of butyllithium (as a 2.5 molar solution in hexane) were added to the clear filtrate. After further stirring for 10 hours, 0.18 mol of trimethylsilyl chloride was again added and the mixture was stirred for a further 10 hours. LiCl was filtered off and the solvent was removed in vacuo. Compound 54 remained as a colorless oil. Yield: 85% of the theoretical yield.

$^1$H-NMR ($CD_2Cl_2$): 7.51 ppm (1 H, d, 7.7 Hz); 7.38 ppm (1 H, d, 7.5 Hz); 7.19 ppm (1 H, t, 7.4 Hz); 7.08 ppm (1 H, t, 7.3 Hz); 3.54 ppm (1H, s); 2.32 ppm (3 H, s); 0.41 ppm (9 H, s, Si(C$\underline{H}_3$)$_3$); 0.0 ppm (9 H, s, Si(C$\underline{H}_3$)$_3$).

Example 66

(Trimethylsilyl-dichloroboranyl-2-methylindene, compound 55)

0.096 mol of the compound 54 was introduced into a 250 ml flask equipped with a dry ice condenser (−30° C.). 0.096 mol of $BCl_3$ was then added and the mixture was stirred at the ambient temperature for 3 hours and at 55° C. for 6 hours. The by-product (CH$_3$)$_3$SiCl was removed; a brown oil remained as the crude product. Distillation from cold trap to cold trap gave the compound 55 in a yield of 75% as a tacky solid.

$^1$H-NMR ($CD_2Cl_2$): 8.09 ppm (1 H, d, 7.9 Hz); 7.37 ppm (1 H, d, 7.6 Hz); 7.26 ppm (1 H, t, 7.5 Hz); 7.16 ppm (1 H, t, 7.5 Hz); 3.89 ppm (1H, s); 2.61 ppm (3 H, s); 0.0 ppm (9 H, s, Si(C$\underline{H}_3$)$_3$. $^{11}$B-NMR ($CD_2Cl_2$): 31.9 ppm.

Example 67

(Tributylstannyl-diethylphosphino-2-methylindene, compound 56)

The procedure was analogous to Example 7.

Example 68

(Diethylphosphino-2-methylindene-zirconium trichloride, compound 57)

The procedure was analogous to Example 8, but instead of toluene, $CH_2Cl_2$ was used as the solvent. The reaction temperature was 25° C. The purification was carried out by Soxhlet extraction with $CH_2Cl_2$. Compound 57 was obtained as an insoluble yellow solid in 78% of the theoretical yield.

Example 69

(($C_2H_5$)$_2$P-BCl$_2$-bridged bis(2-methylindenyl)-zirconium chloride, compound 58)

0.019 mol of compound 55 in 50 ml of toluene was added to a suspension of 0.019 mol of compound 57 in 350 ml of toluene at room temperature.

The reaction mixture was then heated to 80° C. and stirred for 24 hours. After cooling and filtration, 300 ml of hexane were added to the clear, orange-colored solution, after which a heavy orange-colored oil and a clear yellow solution were formed. Concentration and cooling to −25° C. gave the compound rac-58 as a pale yellow powder.

$^{1}$H-NMR: 8.14 ppm (1 H, d, 8.6 Hz); 7.96 ppm (1 H, d, 8.9 Hz); 7.47–7.05 ppm (6 H, various overlapping multiplets) 6.53 ppm (1H, d, 1.9 Hz); 6.47 ppm (1 H, s); 3.0–2.55 ppm (4 H, various overlapping multiplets, P(CH$_2$CH$_3$)$_2$); 2.21 ppm (3 H, s, CH$_3$); 2.08 ppm (3 H, s, CH$_3$); 1.44 ppm (3 H, m, P(CH$_2$CH$_3$)$_2$), 1.07 ppm (3 H, m, P(CH$_2$(CH$_3$)$_2$). $^{31}$P-NMR: 21.4 ppm. $^{11}$B-NMR: −14.7 ppm.

Example 70
(Propene polymerization)

A thoroughly heated 300 ml V4A steel autoclave was charged with 100 ml of dry, oxygen-free toluene and 0.5 ml of a 1 molar triisobutylaluminum/toluene solution. About 1 mol of propene was then transferred into the autoclave. 1 ml of a chlorobenzene solution which comprised 4×10$^{-6}$ mol of dimethylanilinium tetrakis(pentafluorophenyl)borate was added in a pressure sluice to 3.1 ml of a catalyst solution in toluene, which had been preformed at room temperature for 30 minutes and comprised 1×10$^{-6}$ mol of rac[(2-Me-ind)Et$_2$PBCl$_2$(2-Me-ind)ZrCl$_2$] and 0.1 mmol of triisobutylaluminum (TiBA), and the mixture was topped up to 5 ml with toluene. After the catalyst solution had been transferred into the autoclave under pressure, the internal temperature rose from 20° C. to 48° C. in spite of external cooling with dry ice/acetone.

20 minutes after addition of the catalyst, the polymerization was interrupted and the contents of the autoclave were extracted by stirring in 500 ml of ethanol and 50 ml of concentrated aqueous hydrochloric acid for 2 hours. The white polypropylene powder was then isolated by filtration, washed with ethanol and dried at 115° C.

Polymer yield: 11.6 g

Catalyst activity: 34.8 tonnes of i-PP per mole of catalyst and hour The DSC measurement gave, in the 2nd heating up, a melting point T$_m$32 155° C. The NMR measurement gave an isotactility index I.I.=88%

The limiting viscosity [η] measured in ortho-dichlorobenzene (ODCB) at 140° C. was 3.60 dl/g, corresponding to a molecular weight M$_{visc}$=798 kg/mol (calculated by the method of Atkinson et al., Makromol. Chem. (1976), 177, 213).

With rac-52 under comparable experimental conditions at a polymerization temperature of between 10° and 20°, an i-PP was obtained with I.I.=92% and [η]=1.20 dl/g, corresponding to a calculated average molecular weight M$_{visc}$=169 kg/mol.

Example 71
(Ethylene polymerization)

A thoroughly heated 300 ml V4A steel autoclave was charged with 100 ml of dry, oxygen-free toluene and heated up to 100° C. A constant 10 bar was established with ethylene and the catalyst was added by means of a pressure sluice.

5×10$^{-7}$ mol of meso-[(ind)Et$_2$PBCl$_2$(ind)ZrCl$_2$] which had been preformed with 5×10$^{-3}$ mol of MAO in 5 ml of toluene at RT for 15 minutes, were used as the catalyst.

The internal temperature rose to 111° C. during the polymerization.

Polyethylene yield after 30 minutes: 12.1 g

Catalyst activity: 48.4 tonnes of polymer per mole of catalyst and hour

Limiting viscosity in ortho-dichlorobenzene at 140° C.: [η]=0.91 dl/g DSC analysis: T$_m$=136° C.

Example 72

The procedure was as in Example 70, but with the difference that it was carried out under a propene pressure of only 2 bar. The internal temperature rose from 20° C. to 23° C. The melting point of the polypropylene formed in this case was T$_m$=158° C.

What is claimed is:

1. A process for the preparation of a high-melting polyolefin by homo- or copolymerization of one or more monomers from the group consisting of α-olefins having 2 or more C atoms in the presence of an organometallic catalyst which can be activated by a cocatalyst, which comprises employing as the organometallic catalyst a metallocene compound or π complex compound of the formula

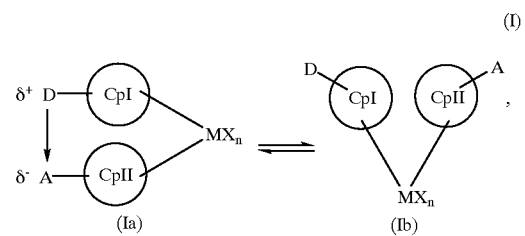

in which

CpI and CpII are two identical or different carbanions having a cyclopentadienyl-containing structure, in which one to all the H atoms can be substituted by identical or different radicals from the group consisting of linear or branch C$_1$–C$_{20}$-alkyl, which can be mono-substituted to completely substituted by halogen, mono- to trisubstituted by phenyl or mono- to trisubstituted by vinyl, C$_6$–C$_{12}$-aryl, halogenoaryl having 6 to 12 C atoms, organometallic substituents, including silyl, trimethylsilyl or ferrocenyl, or one or two can be replaced by D and A, D denotes a donor atom, which can additionally carry substituents and has at least one free electron pair in its bond state, A denotes an acceptor atom, which can additionally carry substituents and has an empty orbital capable of accepting a pair of electrons in its bond state, wherein D and A are linked by a reversible coordinate bond such that the donor group assumes a positive charge and the acceptor group assumes a negative charge, M represents a transition metal of sub-group III, IV, V or VI of the Periodic Table of the Elements, including the lanthanides and actinides, X denotes one anion equivalent and n denotes the number zero, one, two, three or four, depending on the charge of M, or a π complex compound, or metallocene compound of the formula

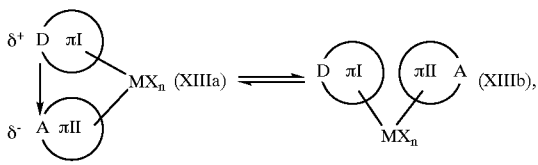

in which
π I and π II represent different charged or electrically neutral π systems which can be fused with one or two unsaturated or saturated five- or six-membered rings,
D denotes a donor atom, which is a substituent of π I or part of the π system of π I and has at least one free electron pair in its bond state,
A denotes an acceptor atom, which is a substituents of π II or part of the π system of π II and has an empty orbital capable of accepting a pair of electrons in its bond state,
wherein D and A are linked by a reversible coordinate bond such that the donor group assumes a positive charge and the acceptor group assumes a negative charge, and where at least one of D and A is part of the associated π system,
wherein D and A in their turn can carry substituents, wherein each π system and each fused-on ring system can contain one or more D or A or D and A and wherein π I and π II in the non-fused or in the fused form, one to all the H atoms of the π system independently of one another can be substituted by identical or different radicals from the group consisting of linear or branched $C_1$–$C_{20}$-alkyl, which can be monosubstituted to completely substituted by halogen, mono- to trisubstituted by phenyl or mono- to trisubstituted by vinyl, $C_6$–$C_{12}$-aryl, halogenoaryl having 6 to 12 C atoms, organometallic substituents, including silyl, trimethylsilyl or ferrocenyl, or one or two can be replaced by D and A, so that the reversible coordinate D→A bond (i) is formed between D and A which are both parts of the π system or the fused-on ring system, or (ii) of which D or A is part of the π system and in each case the other is substituent of the non-fused π system or the fused-on ring system, or (iii) both D and A are such substituents, and in the case of (iii) at least one additional D or A or both is (are) parts of the π system or the fused-on ring system,
M and X have the above meanings and
n denotes the number zero, one, two, three or four, depending on the charges of M and those of π-I and π-II.

2. The process as claimed in claim 1, wherein the metallocene compound or the π complex compound is employed as the catalyst in an amount of $10^1$ to $10^{12}$ mol of monomers per mole of metallocene or π complex compound.

3. The process as claimed in claim 1, wherein the reaction is carried out in the presence of solvents selected from the group consisting of aromatic hydrocarbons, saturated hydrocarbon, aromatic halohydrocarbons and saturated halohydrocarbons.

4. The process as claimed in claim 1, wherein, in the metallocene compound or the π complex compound, the carbanions CpI and CpII or the π system π I denote a cyclopentadienyl skeleton from the group consisting of cyclopentadiene, substituted cyclopentadiene, indene, substituted indene, fluorene and substituted fluorene, in which 1 to 4 substituents from the group consisting of $C_1$–$C_{20}$-alkyl, $C_1$–$C_{20}$-alkoxy, halogen, $C_6$–$C_{12}$-aryl, halogenophenyl, D and A, wherein D and A, are present per cyclopentadiene or fused-on benzene ring, it being possible for fused-on aromatic rings to be partly or completely hydrogenated.

5. The process as claimed in claim 1, wherein, in the metallocene compound, elements selected from the group consisting of N, P, As, Sb, Bi, O, S, Se, Te, F, Cl, Br and I, are present as donor atoms D.

6. The process as claimed in claim 1, wherein, in the metallocene compound, elements selected from the group consisting of B, Al, Ga, In and Tl are present as acceptor atoms A.

7. The process as claimed in claim 1, wherein in the metallocene compound or π complex compound, donor-acceptor bridges selected from the group consisting of

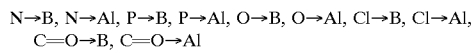

are present.

8. The process as claimed in claim 1, wherein, in the metallocene compound, M represents Sc, Y, La, Sm, Nd, Lu, Ti, Zr, Hf, Th, V, Nb, Ta or Cr.

9. The process as claimed in claim 1, wherein the metallocene compound or π complex compound is employed as a catalyst system together with an aluminoxane, a borane or borate and, optionally, further cocatalysts and/or metal-alkyls.

10. The process as claimed in claim 1, wherein a rearrangement product of said metallocene compound or π complex compound with self-activation, with which, after opening of the D/A bond, the acceptor atom A bonds an X ligand to form a zwitterionic metallocene complex structure or π complex structure, where a positive charge is generated in the transition metal M and a negative charge is generated in the acceptor atom A, and where a further X ligand represents H or substituted or unsubstituted C, in the bond of which to the transition metal M the olefin insertion takes place for the polymerization, preferably 2 X ligands being linked to a chelate ligand, is employed.

11. The process as claimed in claim 1, wherein in said π complex compound D is part of the ring of the associated π system.

12. The process as claimed in claim 1, wherein a reaction product of the formulae (XI(a–d)) of an ionizing agent with said metallocene compound or π complex according to formula (I) or (XIII)

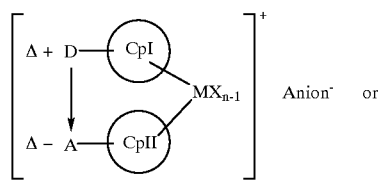

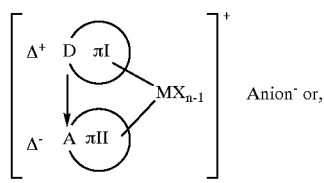

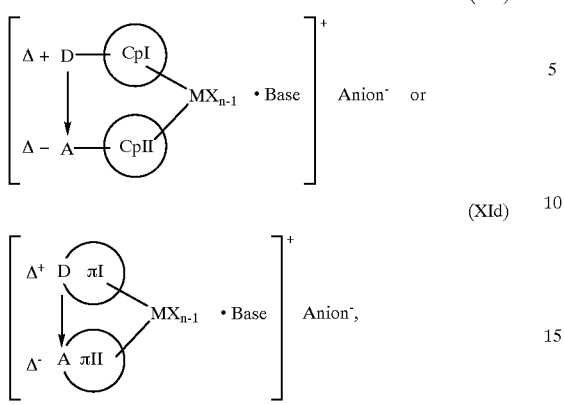

in which
Anion represents the entire bulky, poorly coordinating anion and Base represents a Lewis base, is employed.

13. The process as recited in claim 1, directed to the preparation of a high-melting polyolefin selected form the group consisting of HDPE, LLDPE with butylene, hexene or octene, iPP, and sPP.

14. The process as claimed in claim 1, wherein said process is directed to the preparation of a linear polyethylene having a melting point of 140–160° C.

15. The process according to claim 5, wherein, in the metallocene compound, elements selected from the group consisting of N, P, O and S are present as donor atoms D.

16. The process according to claim 6, wherein, in the metallocene compound, elements selected from the group consisting of B, Al, and Ga, are present as acceptor atoms A.

17. The process according to claim 8, wherein, in the metallocene compound, M represents Ti, Zr, Hf, V, Nb or Ta.

18. The process according to claim 14, wherein said melting point ranges from 142 to 160° C.

19. The process according to claim 18, wherein said melting point ranges from 144 to 160° C.

20. The process according to claim 19, wherein said melting point ranges from 146 to 160° C.

21. A linear polyethylene having a melting point of 140 to 160° C., which is prepared by polymerization of ethylene in the presence of an organometallic catalyst which can be activated by a cocatalyst, which comprises employing as the organometallic catalyst a metallocene pound or π complex compound of the formula

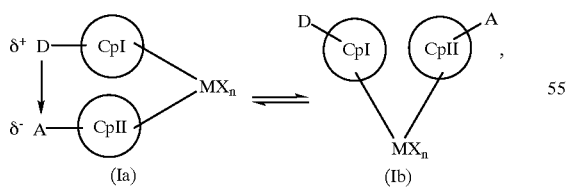

in which
CpI and CpII are two identical or different carbanions having a cyclopentadienyl-containing structure, in which one to all the H atoms can be substituted by identical or different radicals from the group consisting of linear or branched $C_1$–$C_{20}$-alkyl, which can be monosubstituted to completely substituted by halogen,
mono- to trisubstituted by phenyl or mono- to trisubstituted by vinyl, $C_6$–$C_{12}$-aryl, halogenoaryl having 6 to 12 C atoms, organometallic substituents, including silyl, trimethylsilyl or ferrocenyl, or one or two can be replaced by D and A, D denotes a donor atom, which can additionally carry substituents and has at least one free electron pair in its bond state, A denotes an acceptor atom, which can additionally carry substituents and has an empty orbital capable of accepting a pair of electrons in its bond state,
wherein D and A are linked by a reversible coordinate bond such that the donor group assumes a positive charge and the acceptor group assumes a negative charge, M represents a transition metal of sub-group III, IV, V or VI of the Periodic Table of the Elements, including the lanthanides and actinides, X denotes one anion equivalent and N denotes the number zero, one, two, three or four, depending on the charge of M, or a π complex compound, or metallocene compound of the formula

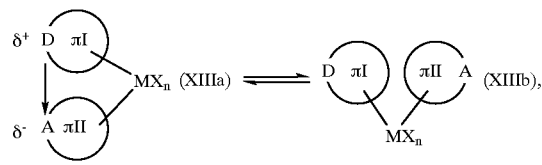

in which
πI and πII represent different charged or electrically neutral π systems which can be fused with one or two unsaturated or saturated five- or six-membered rings, D denotes a donor atom, which is a substituent of πI or part of the π system of πI and has at least one free electron pair in its bond state, A denotes an acceptor atom, which is a substituent of πII or part of the π system of πII and has an empty orbital capable of accepting a pair of electrons in its bond state,
wherein D and A are linked by a reversible coordinate bond such that the donor group assumes a positive charge, and the acceptor group assumes a negative charge, and where at least one of D and A is part of the associated π system,
wherein D and A in their turn can carry substituents,
wherein each π system and each fused-on ring system can contain one or more D or A or D and A and
wherein πI and πII in the non-fused or in the fused form, one to all the H atoms of the π system independently of one another can be substituted by identical or different radicals from the group consisting of linear or branched $C_1$–$C_{20}$-alkyl, which can be monosubstituted to completely substituted by halogen, mono- to trisubstituted by phenyl or mono- to trisubstituted by vinyl, $C_6$–$C_{12}$-aryl, halogenoaryl having 6 to 12 C atoms, organometallic substituents, including silyl, trimethylsilyl or ferrocenyl, or one or two can be replaced by D and A, so that the reversible coordinate D→A bond (i) is formed between D and A which are both parts of the π system or the fused-on ring system, or (ii)

of which D or A is part of the π system and in each case the other is substituent of the non-fused π system or the fused-on ring system, or (iii) both D and A are such substituents, and in the case of (iii) at least one additional D or A or both is (are) parts of the π system or the fused-on ring system, M and X have the above meanings and n denotes the number zero, one, two, three or four depending on the charges of M and those of π-I and π-II.

22. The polyethylene according to claim 21, wherein said melting point ranges from 142 to 160° C.

23. The polyethylene according to claim 22, wherein said melting point ranges from 144 to 160° C.

24. The polyethylene according to claim 23, wherein said melting point ranges from 146 to 160° C.

\* \* \* \* \*